(12) United States Patent
Patil

(10) Patent No.: US 11,293,931 B2
(45) Date of Patent: *Apr. 5, 2022

(54) QUANTITATIVE PROFILING OF PROGESTERONE METABOLITES FOR THE PREDICTION OF SPONTANEOUS PRETERM DELIVERY

(71) Applicant: Indiana University Research and Technology Corporation, Indianapolis, IN (US)

(72) Inventor: Avinash Shivaputrappa Patil, Zionsville, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 259 days.

This patent is subject to a terminal disclaimer.

(21) Appl. No.: 16/576,160

(22) Filed: Sep. 19, 2019

(65) Prior Publication Data
US 2020/0081013 A1   Mar. 12, 2020

Related U.S. Application Data

(63) Continuation-in-part of application No. 16/099,017, filed as application No. PCT/US2017/030759 on May 3, 2017.

(Continued)

(51) Int. Cl.
G01N 33/74   (2006.01)
G01N 33/68   (2006.01)

(52) U.S. Cl.
CPC ......... G01N 33/689 (2013.01); G01N 33/743 (2013.01); G01N 2333/471 (2013.01);
(Continued)

(58) Field of Classification Search
None
See application file for complete search history.

(56) References Cited

U.S. PATENT DOCUMENTS

| 2014/0093900 A1 | 4/2014  | Kushnir et al. |
| 2015/0376709 A1 | 12/2015 | Dong et al.    |
| 2016/0069891 A1 | 3/2016  | Equils et al.  |

FOREIGN PATENT DOCUMENTS

| WO | 2012075150 A2 | 6/2012 |
| WO | 2014144129 A2 | 9/2014 |
| WO | 2015091591 A1 | 6/2015 |

OTHER PUBLICATIONS

Soldin et al., "Steroid hormone levels in pregnancy and 1 year postpartum using isotope dilution tandem mass spectrometry", Fertility and Sterility, 84(3): pp. 701-710, Sep. 2005. (Year: 2005).*

(Continued)

Primary Examiner — Rebecca M Giere
(74) Attorney, Agent, or Firm — Stinson LLP

(57) ABSTRACT

Disclosed are methods for identifying a pregnant female who is susceptible to spontaneous preterm delivery. In particular, disclosed are methods for identifying a pregnant female who is susceptible to spontaneous preterm delivery based on ratios of steroids in samples obtained from the pregnant female. Further, the methods can include treating the pregnant female identified susceptible to spontaneous preterm delivery.

20 Claims, 10 Drawing Sheets

Related U.S. Application Data

(60) Provisional application No. 62/332,174, filed on May 5, 2016.

(52) U.S. Cl.
CPC ............... *G01N 2333/4727* (2013.01); *G01N 2333/4745* (2013.01); *G01N 2333/575* (2013.01); *G01N 2800/368* (2013.01)

(56) References Cited

OTHER PUBLICATIONS

Brown et al., Plasma Deoxycorticosterone in Normal and Abnormal Human Pregnancy1; J Clin Endocrinol Metab (1972); vol. 35, No. 5, pp. 736-742.
Gaikwad N. W., Ultra Performance Liquid Chromatography-Tandem Mass Spectrometry Method for Profiling of Steroid Metabolome in Human Tissue; Anal. Chem., 2013, vol. 85, No. 10, pp. 4951-4960.
Parker et al., Hormone production during pregnancy in the primigravid patient. II. Plasma Levels of deoxycorticosterone throughout pregnance of normal women and women who developed pregnancy-induced hypertension; Am J Obstet Gynecol., 1980, vol. 138, No. 6, pp. 626-631.
Saade et al., Development and validation of a spontaneous preterm delivery predictor in asymptomatic women; Am J of Obstetrics & Gynecology; 2016, pp. 633.e1.

\* cited by examiner

QUANTITATIVE PROFILING OF PROGESTERONE METABOLITES FOR THE PREDICTION OF SPONTANEOUS PRETERM DELIVERY

CROSS-REFERENCE TO RELATED APPLICATION

This application is a continuation-in-part application of U.S. patent application Ser. No. 16/099,017 (published as U.S. Publication No. 2019/0137507), filed Nov. 5, 2018, which claims priority from U.S. Patent Application Ser. No. 62/332,174, filed May 5, 2016, each of which is incorporated herein by reference in its entirety.

BACKGROUND OF THE DISCLOSURE

The present disclosure relates generally to the risk assessment of preterm delivery in a pregnant female. More particularly, the present disclosure relates to the prediction of spontaneous preterm delivery in a pregnant female using ratios of endogenous steroids in samples obtained from a pregnant female.

Preterm birth is a major public health problem, leading to lifelong morbidities in premature newborns and high expenditures for health care systems and insurance companies. Each year, an estimated 15 million babies are born preterm (before 37 weeks gestation) according to the World Health Organization. Globally, preterm birth is the leading cause of newborn deaths (babies in the first four weeks of life) and the second leading cause of death in children under five years. Nationally, preterm delivery prior to 32 weeks gestation is associated with an 80-fold increase in infant mortality compared to women delivery between 39-41 weeks. Complications arising from preterm birth include acute respiratory, gastrointestinal, immunologic, central nervous system, hearing, and vision problems, as well as longer-term motor, cognitive, visual, hearing, behavioral, social-emotional, health, and growth problems. Many survivors face a lifetime of disability, including learning disabilities and visual and hearing problems.

If a pregnant woman is determined to be at risk for preterm birth, health care providers can implement various clinical strategies that may include surgical procedures such as cervical cerclage and cervical pessaries, preventive medications, restrictions on sexual activity and/or other physical activities, and alterations of treatments for chronic conditions that increase the risk of preterm labor.

Women identified as high-risk can be scheduled for more intensive surveillance and interventions. Very few technologies exist to identify women at risk for preterm birth who could benefit from additional interventions. The tools that are currently available have limited sensitivity/specificity or identify molecular changes associated with preterm labor without offering any interventions to mitigate this process. Current strategies for risk assessment are based on the obstetric and medical history and clinical examination, but these strategies are only able to identify a small percentage of women who are at risk for preterm delivery. Clinically available tools for risk assessment are available in the mid-second trimester, after the period of maximal benefit from interventions. Reliable early identification of risk for preterm birth would allow for appropriate monitoring and clinical management to prevent preterm delivery.

Further, only one medication has been approved by the FDA for the prevention of recurrent spontaneous preterm delivery: 17α-hydroxyprogesterone caproate (HPC). A landmark prospective trial of HPC in women with a prior history of spontaneous preterm birth (sPTB) demonstrated a 30-40% reduction in the risk of recurrent sPTB. However, 40% of preterm deliveries occur in first-time pregnancies and 70% of pregnant women delivering prematurely in their second pregnancy had full-term deliveries in their first pregnancy. Further, HPC is not uniformly effective in all patients, and identification of biomarkers to predict therapeutic response is still in progress. Interestingly, a metabolite of HPC termed monohydroxylated HPC (HPC-OH) has recently been tested and found to have improved tocolytic properties relative to the parent molecule. It is possible that this molecule may have a more pronounced action on the HPA axis.

Accordingly, there exists a need for alternative tools for assessing risk factors in the occurrence of spontaneous preterm delivery.

BRIEF DESCRIPTION OF THE DISCLOSURE

The present disclosure is generally directed to methods for identifying whether a pregnant female is susceptible to spontaneous preterm delivery. More particularly, the present disclosure is directed to methods for identifying whether a pregnant female is susceptible to spontaneous preterm delivery based on ratios of DOC/16αOHP and ratios of DOC/11-deoxycortisol. It has been found that the methods of the present disclosure are effective at identifying susceptibility of spontaneous preterm delivery in both women with a history of preterm delivery and in women without a history of preterm delivery.

Additionally, the present disclosure is directed to treating the pregnant female once identified as being susceptible to spontaneous preterm delivery. Particularly, the present disclosure is directed to administering an effective amount of 17α-hydroxyprogesterone caproate (HPC), a metabolite, or derivative thereof, to a pregnant female identified as susceptible to spontaneous preterm delivery.

In one aspect, the present disclosure is directed to a method for identifying a pregnant female who is susceptible to spontaneous preterm delivery, the method comprising: obtaining a sample from the pregnant female; determining a concentration of a first steroid; determining a concentration of at least one additional steroid; calculating a ratio of the first steroid and at least one additional steroid; and identifying the pregnant female as being susceptible to spontaneous preterm delivery when the ratio in the sample is reduced below a threshold value.

In one aspect, the present disclosure is directed to a method for identifying a pregnant female who is susceptible to spontaneous preterm delivery, the method comprising: obtaining a sample from the pregnant female; determining a concentration of deoxycorticosterone (DOC); determining a concentration of 16α-hydroxyprogesterone (16αOHP); calculating a ratio of DOC/16αOHP; and identifying the pregnant female as being susceptible to spontaneous preterm delivery when the DOC/16αOHP ratio in the sample is reduced below a threshold value.

In another aspect, the present disclosure is directed to a method for identifying a pregnant female who is susceptible to spontaneous preterm delivery, the method comprising: obtaining a sample from the pregnant female; determining a concentration of deoxycorticosterone (DOC); determining a concentration of 11-deoxycortisol; calculating a ratio of DOC/11-deoxycortisol; and identifying the pregnant female as being susceptible to spontaneous preterm delivery when the DOC/11-deoxycortisol ratio in the sample is reduced below a threshold value.

In yet another aspect, the present disclosure is directed to a method for treating a pregnant female susceptible to spontaneous preterm delivery. The method comprises: determining a ratio of at least two steroids in the pregnant female by: obtaining a sample from the pregnant female; detecting a concentration of a first steroid selected from the group consisting of deoxycorticosterone, corticorterone, 18-hydroxycortiosterone, aldosterone, deoxycortisol, cortisol, and combinations thereof in the sample; detecting a concentration of at least a second steroid in the sample, wherein the second steroid is different from the first steroid; and detecting a ratio of the first steroid to the at least second steroid. If the ratio of the first steroid to the at least second steroid is less than 0.2, then administering an effective amount of a compound selected from the group consisting of 17α-hydroxyprogesterone caproate (HPC), monohydrogenated HPC (HPC-OH), atosiban, nifedipine, terbutaline, eplerenone, and derivatives thereof.

In accordance with the present disclosure, methods have been discovered that surprisingly allow for identifying and treating a pregnant female who is susceptible to spontaneous preterm delivery. Significantly, the methods of the present disclosure allow for determining whether a pregnant female is susceptible to having a spontaneous preterm delivery based on samples obtained weeks, and even months, prior to delivery. The methods of the present disclosure significantly allow for the identification of a pregnant female as being susceptible for spontaneous preterm birth allowing for appropriate monitoring and clinical management to prevent spontaneous preterm delivery.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1:
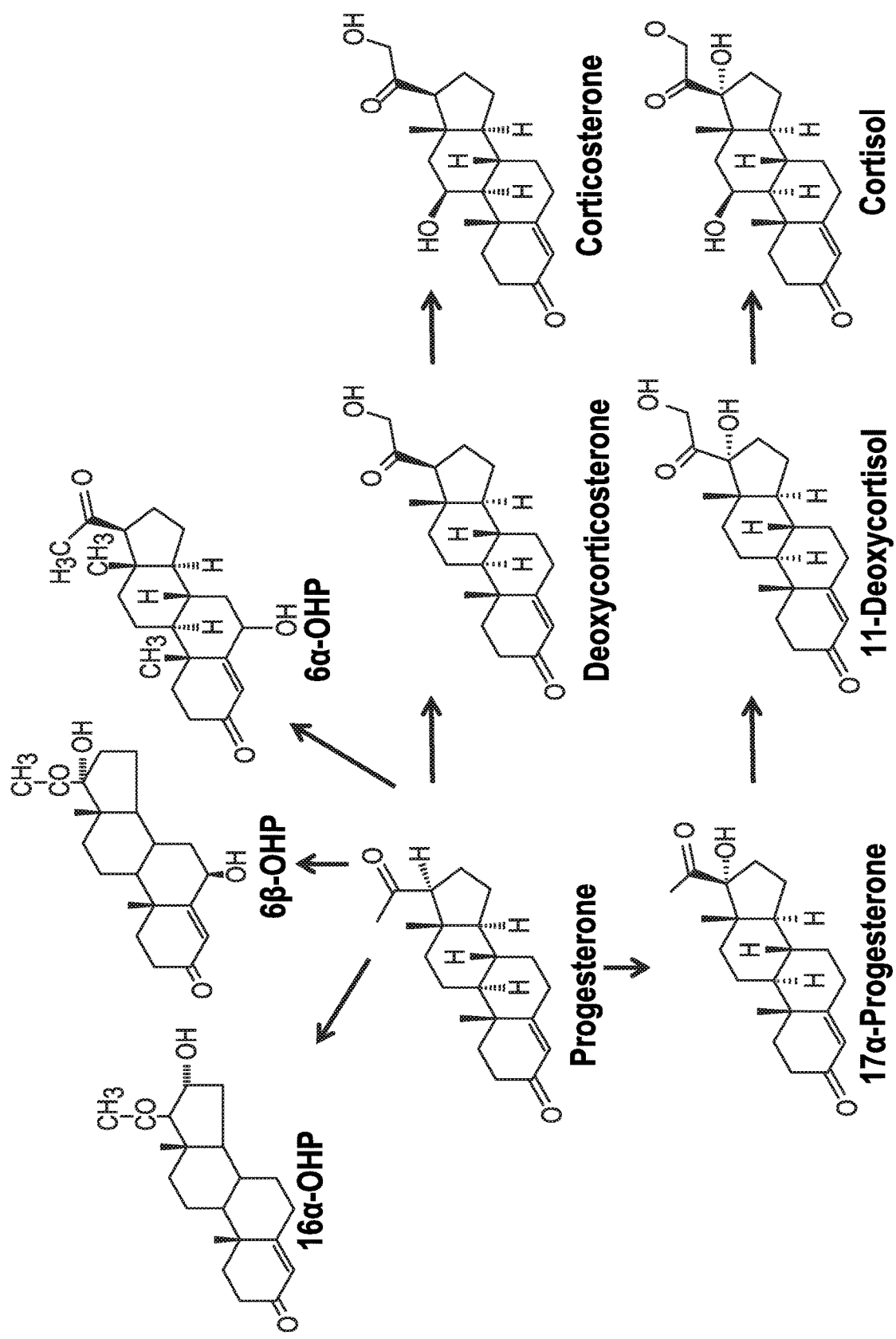
FIG. 1 is a flowchart of the metabolism of progesterone. Briefly, progesterone is metabolized into several derivatives, including 16α-hydroxyprogesterone (16α-OHP), deoxycorticosterone (DOC), and 11-deoxycortisone.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the suitable methods and materials are described below.

As used in this application, including the appended claims, the singular forms "a," "an," and "the" include plural references, unless the content clearly dictates otherwise, and are used interchangeably with "at least one" and "one or more."

As used herein, "spontaneous preterm delivery" and "spontaneous preterm birth" are used interchangeably herein to refer to delivery or birth at a gestational age less than 37 completed weeks. Other commonly used subcategories of spontaneous preterm birth delineate moderately preterm (birth at 33 to 37 weeks of gestation), very preterm (birth at less than 33 weeks of gestation), and extremely preterm (birth at less than 28 weeks of gestation).

A number of methods can be used to determine the amount of a biomarker, including mass spectrometry approaches, such as MS/MS, LC-MS/MS, multiple reaction monitoring (MRM) or SRM and product-ion monitoring (PIM) and also including antibody based methods such as immunoassays such as Western blots, enzyme-linked immunosorbant assay (ELISA), immunopercipitation, immunohistochemistry, immunofluorescence, radioimmunoassay, dot blotting, and FACS.

A detectable label can be used in the assays described herein for direct or indirect detection of the biomarkers in the methods of the present disclosure. A wide variety of detectable labels can be used, with the choice of label depending on the sensitivity required, ease of conjugation with the antibody, stability requirements, and available instrumentation and disposal provisions. Those skilled in the art are familiar with selection of a suitable detectable label based on the assay detection of the biomarkers in the methods of the present disclosure. Suitable detectable labels include, but are not limited to, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), enzymes (e.g., luciferase, horseradish peroxidase, alkaline phosphatase, etc.), nanoparticles, biotin, digoxigenin, metals, and the like.

The predictive ability of a model can be evaluated according to its ability to provide a quality metric, e.g. AUROC (area under the ROC curve) or accuracy, of a particular value, or range of values. Area under the curve measures are useful for comparing the accuracy of a classifier across the complete data range.

Classifiers with a greater AUC have a greater capacity to classify unknowns correctly between two groups of interest. In some embodiments, a desired quality threshold is a predictive model that will classify a sample with an accuracy of at least 0.5, at least 0.55, at least 0.6, at least 0.7, at least 0.75, at least 0.8, at least 0.85, at least 0.9, at least 0.95, or higher. As an alternative measure, a desired quality threshold can refer to a predictive model that will classify a sample with an AUC of at least 0.7, at least 0.75, at least 0.8, at least 0.85, at least 0.9, or higher.

The term "measurement" suitably comprises a qualitative, semi-qualitative or a quantitative measurement of ratios of steroids selected from progesterone, 16α-hydroxyprogesterone, 6β-hydroxyprogesterone, 6α-hydroxyprogesterone, 17-hydroxyprogesterone, 11-deoxycortisol, cortisol, 11-deoxycorticosterone, 17-deoxycortisol, androstenedione, testosterone, estradiol, 20α-dihydroprogesterone, 17α,20α-dihydroxyprogesterone, and isopregnanolone in a sample. In a suitable embodiment the measurement is a semi-quantitative measurement, i.e., it is determined whether the ratios of steroids selected from progesterone, 16α-hydroxyprogesterone, 6β-hydroxyprogesterone, 6α-hydroxyprogesterone, 17-hydroxyprogesterone, 11-deoxycortisol, cortisol, 11-deoxycorticosterone, 17-deoxycortisol, androstenedione, testosterone, estradiol, 20α-dihydroprogesterone, 17α,20α-dihydroxyprogesterone, isopregnanolone are above or below a cut-off (threshold) value. As the skilled artisan will appreciate, in a Yes—(presence) or No—(absence) assay, the assay sensitivity is usually set to match the cut-off value. A cut-off value can for example be determined from the testing of a group of healthy individuals. Suitably, the cut-off is set to result in a specificity of 90%, also suitable, the cut-off is set to result in a specificity of 95%, or also suitable, the cut-off is set to result in a specificity of 98%. A value below the cut-off value can for example be indicative for spontaneous preterm delivery. In particular, a value below the cut-off value can for example be indicative for spontaneous preterm delivery at less than 37 weeks gestation. In particular, a value below the cut-off value can for example be indicative for spontaneous preterm delivery at less than 34 weeks gestation. In particular, a value below the cut-off value can for example be indicative for spontaneous preterm delivery at less than 32 weeks gestation. In particular, a value below the cut-off value can for example be indicative for spontaneous preterm delivery at less than 30 weeks gestation, including less than 28 weeks, including less than 22 weeks, and including less than 16 weeks gestation. Alternatively, a value above the cut-off value can for example be indicative for less susceptibility to spontaneous preterm delivery. In particular, a value above the cut-off value can for example be indicative for less susceptibility to spontaneous preterm delivery at less than 37 weeks gestation. In particular, a value above the cut-off value can for example be indicative for less susceptibility to spontaneous preterm delivery at less than 34 weeks gestation. In particular, a value above the cut-off value can for example be indicative for less susceptibility to spontaneous preterm delivery at less than 32 weeks gestation. In particular, a value above the cut-off value can for example be indicative for less susceptibility to spontaneous preterm delivery at less than 30 weeks gestation.

In another suitable embodiment, the cut-off is set to result in a sensitivity of 90%, also suitable, the cut-off is set to result in a sensitivity of 95%, or also suitable, the cut-off is set to result in a sensitivity of 98%.

It has surprisingly been determined that ratios of steroids selected from combinations of progesterone, 16α-hydroxyprogesterone, 6β-hydroxyprogesterone, 6α-hydroxyprogesterone, 17-hydroxyprogesterone, 11-deoxycortisol, cortisol, 11-deoxycorticosterone, 17-deoxycortisol, androstenedione, testosterone, estradiol, 20α-dihydroprogesterone, 17α,20α-dihydroxyprogesterone, and isopregnanolone measured in samples obtained from patients can be used to identify whether a subject is susceptible to spontaneous preterm delivery. Statistical models permit ROC curve analysis of the multi marker assay, and the results confirm the diagnostic accuracy. Significantly, none of the compounds when analyzed alone indicates spontaneous preterm delivery.

Well-known mathematical methods for analyzing the ratios of combinations of progesterone, 16α-hydroxyprogesterone, 6β-hydroxyprogesterone, 6α-hydroxyprogesterone, 17-hydroxyprogesterone, 11-deoxycortisol, cortisol, 11-deoxycorticosterone, 17-deoxycortisol, androstenedione, testosterone, estradiol, 20α-dihydroprogesterone, 17α,20α-dihydroxyprogesterone, and isopregnanolone employ methods like, discriminant analysis (DA) (i.e., linear-, quadratic-, regularized-DA), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting/Bagging Methods), Generalized Linear Models (i.e., Logistic Regression), Principal Components based Methods (i.e., SIMCA), Generalized Additive Models, Fuzzy Logic based Methods, Neural Networks and Genetic Algorithms based Methods.

Accuracy of a risk assessment method is best described by its receiver-operating characteristics (ROC). The ROC graph is a plot of all of the sensitivity/specificity pairs resulting from continuously varying the decision thresh-hold over the entire range of data observed. Diagnostic accuracy measures the test's ability to correctly distinguish two different conditions of the subjects being investigated such as, for example, health and disease. The ROC plot depicts the overlap between the two distributions by plotting the sensitivity versus 1-specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1-specificity [defined as (number of false-positive results)/(number of true-negative+number of false-positive results)]. It is an index of specificity and is calculated entirely from the unaffected subgroup. Because the true- and false-positive fractions are calculated entirely separately using the test results from two different subgroups, the ROC plot is independent of the prevalence of disease in the sample.

Each point on the ROC plot represents a sensitivity/1-specificity pair corresponding to a particular decision threshold. A test with perfect discrimination (no overlap in the two distributions of results) has a ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is remedied by reversing the criterion for "positivity" from "greater than" to "less than" or vice versa.) Qualitatively, the closer the plot is to the upper left corner, the higher the overall accuracy of the test. One particularly suitable way to quantify the diagnostic accuracy of a laboratory test is to express its performance by a single number. Such an overall parameter, e.g., is the so-called "total error" or alternatively the "area under the curve=AUC". The most common global measure is the area under the ROC plot. By convention, this area is always ≥0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

In accordance with the present disclosure, methods for identifying pregnant female subjects susceptible to spontaneous preterm delivery are disclosed. In particular, ratios of steroids selected from progesterone, 16α-hydroxyprogesterone, 6β-hydroxyprogesterone, 6α-hydroxyprogesterone, 17-hydroxyprogesterone, 11-deoxycortisol, cortisol, 11-deoxycorticosterone, 17-deoxycortisol, androstenedione, testosterone, estradiol, 20α-dihydroprogesterone, 17α,20α-dihydroxyprogesterone, isopregnanolone, and combinations thereof, allow for identifying whether a pregnant female is susceptible to spontaneous preterm delivery. In one particular embodiment, the cortexone (deoxycorticosterone (DOC))/isopregnalone ratio in the first and second trimester is predictive of spontaneous preterm delivery. In another particular embodiment, the cortexone (deoxycorticosterone (DOC))/16α-hydroxyprogesterone ratio in the second trimester is predictive of spontaneous preterm delivery. In yet another particular embodiment, the cortexone (deoxycorticosterone (DOC))/cortexolone (11-deoxycortisol) ratio in the third trimester is predictive of spontaneous preterm delivery.

In one aspect, the present disclosure is directed to a method for identifying a pregnant female who is susceptible to spontaneous preterm delivery. The method includes obtaining a sample from the pregnant female; determining a concentration of a first steroid; determining a concentration of at least one additional steroid; calculating a ratio of the first steroid and the at least one additional steroid; and identifying the pregnant female as being susceptible to spontaneous preterm delivery when the ratio in the sample is reduced below a threshold value.

By way of example, a pregnant female can be identified as being susceptible to spontaneous preterm delivery if a ratio of DOC/16αOHP is reduced below a threshold value of 0.2. In another example, a pregnant female can be identified as being susceptible to spontaneous preterm delivery if a ratio of DOC/11-deoxycortisol is reduced below a threshold value of 0.18.

As used herein, "at least one additional steroid" refers to a second steroid, a third steroid, a fourth steroid, and so-forth, including combinations of the second steroid, the third steroid, the fourth steroid, and so-forth. Thus, in one embodiment, the ratio can be calculated between the first steroid and the second steroid, for example. In another embodiment, the ratio can be calculated between the first steroid and the second steroid and the third steroid, for example. In another embodiment, the ratio can be calculated between the first steroid and the second steroid, the third steroid, the fourth steroid, and so-forth.

Particularly suitable steroids include progesterone, 16α-hydroxyprogesterone, 6β-hydroxyprogesterone, 6α-hydroxyprogesterone, 17-hydroxyprogesterone, 11-deoxycortisol, cortisol, 11-deoxycorticosterone, 17-deoxycortisol, androstenedione, testosterone, estradiol, 20α-dihydroprogesterone, 17α,20α-dihydroxyprogesterone, and isopregnanolone.

The method can further include determining a change in a concentration of at least one additional biomarker selected from insulin-like growth factor binding protein 4, sex-hormone binding globulin (SHBG), lipopolysaccharide-binding protein (LBP), lipopolysaccharide-binding protein (LBP) precursor, prothrombin (THRB), complement component C5 (C5 or CO5), plasminogen (PLMN), complement component C8 gamma chain (C8G or CO8G), Complement factor B, Ectonucleotide pyrophosphatase/phosphodiesterase family member 2, Gelsolin, N-acetylmuramoyl-L-alanine amidase, N-acetylmuramoyl-L-alanine amidase precursor, Hyaluronan-binding protein 2, BPI fold-containing family B member 1, complement component C8 alpha chain, apolipoprotein A-II, Ectonucleotide pyrophosphatase/phosphodiesterase family member 2, profiling-1, pro-neuropeptide Y, complement component C8 beta chain, coagulation factor XIIII B chain, N-acetylmuramoyl-L-alanine amidase, inter-alpha-trypsin inhibitor heavy chain H4, inter-alpha-trypsin inhibitor heavy chain H3 preproprotein, leucyl-cystinyl aminopeptidase, alpha-2-HS-glycoprotein, 5'-AMP-activated protein kinase subunit gamma-3, afamin precursor, alpha-1-antichymotrypsin precursor, alpha-1B-glycoprotein precursor, alpha-2-antiplasmin isoform a precursor, alpha-2-HS-glycoprotein preproprotein, alpha-2-HS-macroglobulin precursor, angiotensinogen preproprotein, antithrombin-III precursor, apolipoprotein A-II prepropro-tein, apolipoprotein A-IV precursor, apolipoprotein B-100 precursor, apolipoprotein C-I precursor, apolipoprotein C-II precursor, apolipoprotein C-III precursor, apolipoprotein E precursor, ATP-binding cassette sub-family D member 4, ATP-binding cassette sub-family F member 3, beta-2-glycoprotein 1 precursor, beta-Ala-His dipeptidase precursor, biotinidase precursor, carboxypeptidase B2 preproprotein, carboxypeptidase N catalytic chain precursor, carboxypeptidase N subunit 2 precursor, catalase, ceruloplasmin precursor, cholinesterase precursor, clusterin preproprotein, coagulation factor IX preproprotein, coagulation factor VII isoform a, coagulation factor VII isoform a preproprotein, coagulation factor X preproprotein, coagulation factor XIII B chain, coiled-coil domain-containing protein 13, complement C1q subcomponent subunit A precursor, complement C1q subcomponent subunit B precursor, complement C1q subcomponent subunit C precursor, complement C1r subcomponent precursor, complement C1s subcomponent precursor, complement C2 isoform 3, complement C3 precursor, complement C4-A isoform 1, complement C5 preproprotein, component C6 precursor, component C7 precursor, component C8 alpha chain precursor, complement component C9 precursor, complement factor B preproprotein, complement factor H isoform a precursor, complement factor H isoform b precursor, complement factor H H-related protein 1 precursor, complement factor 1 preproprotein, conserved oligomeric Golgi complex subunit 6 isoform, corticosteroid-binding globulin precursor, C-reactive protein precursor, dopamine beta-hydroxylase precursor, double-stranded RNA-specific editase B2, dual oxidase 2 precursor, FERM domain-containing protein 8, fetuin-B precursor, ficolin-3 isoform 1 precursor, gastric intrinsic factor precursor, gelsolin isoform d, glutathione peroxidase 3 precursor, hemopexin precursor, heparin cofactor 2 precursor, hepatocyte cell adhesion molecule precursor, hepatocyte growth factor activator preproprotein, histidine-rich glycoprotein precursor, hyaluronan-binding protein 2 isoform 1 preproprotein, inactive caspase-12 insulin-degrading enzyme isoform 1, insulin-like growth factor-binding protein complex acid labile subunit isoform 2 precursor, inter-alpha-trypsin inhibitor heavy chain H1 isoform a precursor, inter-alpha-trypsin inhibitor heavy chain H2 precursor, inter-alpha-trypsin inhibitor heavy chain H4 isoform 1 precursor, kallistatin precursor, kininogen-1 isoform 2 precursor, leucine-rich alpha-2-glycoprotein precursor, lumican precursor, m7GpppX diphosphatase, matrix metalloproteinase-19 isoform 1 preproprotein, MBT domain-containing protein 1, monocyte differentiation antigen CD14 precursor, pappalysin-1 preproprotein, phosphatidylinositol-glycan-specific phospholipase D precursor, pigment epithelium-derived factor precursor, plasma kallikrein preproprotein, plasma protease C1 inhibitor precursor, plasminogen isoform 1 precursor, platelet basic protein preproprotein, platelet glycoprotein V precursor, pregnancy zone protein precursor, pregnancy-specific beta-1-glycoprotein 5, pregnancy-specific beta-1-glycoprotein 5 precursor, pregnancy-specific beta-1-glycoprotein 6, pregnancy-specific beta-1-glycoprotein 6 precursor, pregnancy-specific beta-1-glycoprotein 7, pregnancy-specific beta-1-glycoprotein 8, pregnancy-specific beta-1-glycoprotein 9, pregnancy-specific beta-1-glycoprotein 11, pregnancy-specific beta-1-glycoprotein 2, pregnancy-specific beta-1-glycoprotein 3, pregnancy-specific beta-1-glycoprotein 4, progesterone-induced-blocking factor 1, protein AMBP preproprotein, protein CBFA2T2 isoform MTGR1b, protein FAM98C, protein NLRC3, protein Z-dependent protease inhibitor precursor, prothrombin preproprotein, putative hydroxypyruvate isomerase isoform 1, ras-like protein family member 10A precursor, ras-related GTP-binding protein A, retinol-binding protein 4 precursor, sex hormone-binding globulin isoform 1 precursor, sex hormone-binding globulin isoform 4 precursor, signal transducer and activator of transcription 2, spectrin beta chain non-erythrocytic 1, stabilin-1 precursor, succinate semialdehyde dehydrogenase mitochondrial, tetranectin precursor, THAP domain-containing protein 6, thyroxine-binding globulin precursor, tripartite motif-containing protein 5, vitamin D-binding protein isoform 1 precursor, vitronectin precursor, zinc finger protein 142, attractin isoform 2 preproprotein, transforming growth factor-beta-induced protein ig-h3 precursor, transthyretin precursor, uncharacterized protein C3orf20, beta-2-microglobulin precursor, bone marrow proteoglycan isoform 1 preproprotein, chorionic gonadotropin beta polypeptide 8 precursor, chorionic somatomammotropin hormone 2 isoform 2 precursor, macrophage colony-stimulating factor 1 receptor precursor, zinc-alpha-2-glycoprotein precursor, PAN-PSG, complement component C6 precursor, EGF-containing fibulin-like extracellular matrix protein 1, and disintegrin and metalloproteinase domain-containing protein 12. Ratios can be obtained by pairing these biomarkers with the steroids described above. Methods of measuring concentrations of these biomarkers in pregnant females are described Saade et al., Am J of Obstetrics & Gynecology, May 2016 633e1-633e24, which is incorporated by reference to the extent it is consistent herewith.

The method can further include determining a change in nucleic acids of the pregnant female. More particularly, nucleic acids for combinatorial use in the methods of the present disclosure can include nucleic acid primers and/or probes that bind with specific nucleic acid sequences as well as the nucleic acids that are increased or decreased in concentration in pregnant females that are susceptible to preterm delivery. In suitable embodiments, the nucleic acids can include cell free plasma (CFP) RNA such as disclosed in U.S. Publication No. 2015/0376709 to Dong et al. (Sep. 11, 2015), which is incorporated by reference to the extent it is consistent herewith. In other embodiments, the nucleic acids can include cell free fetal DNA ("fetal fraction").

The sample can be obtained at gestational times ranging from about 8 weeks to about 41 weeks. In one embodiment, the sample is obtained at a gestational age ranging from about 8 weeks to about 24 weeks. In another embodiment, the sample is obtained at a gestational age ranging from about 25 weeks to about 35 weeks. In one embodiment, the sample is obtained at less than 34 weeks gestation. In another embodiment, the sample is obtained at less than 32 weeks gestation. In another embodiment, the sample is obtained at less than 30 weeks.

In one embodiment, the sample is obtained from the pregnant female in the first trimester, generally considered from the date of the last menstrual period to 13 weeks. In one embodiment, the sample is obtained from the pregnant female in the second trimester, generally considered from about the $14^{th}$ week to about the $27^{th}$ week. In one embodiment, the sample is obtained from the pregnant female in the third trimester, generally considered from about the $28^{th}$ week to about the $42^{nd}$ week.

Suitable samples include a plasma sample, a serum sample, a whole blood sample, a salivary sample and a urine sample. Plasma samples and urine samples are particularly suitable.

The method can further include analyzing at least one pregnancy risk factor. Suitable risk factors include, for example, age, prior pregnancy, history of previous low birth weight or preterm delivery, multiple 2nd trimester spontaneous abortion, prior first trimester induced abortion, preeclampsia, familial and intergenerational factors, history of infertility, nulliparity, placental abnormalities, cervical and uterine anomalies, gestational bleeding, intrauterine growth restriction, in utero diethylstilbestrol exposure, multiple gestations, infant sex, short stature, low prepregnancy weight/low body mass index, diabetes, hypertension, hypothyroidism, asthma, education level, tobacco use, and urogenital infections.

Suitable methods for determining concentrations of steroids and biomarkers can be, for example, immunoassays, chromatography, mass spectrometry, amplification, microarray analysis, and combinations thereof. A particularly suitable chromatography-mass spectrometry method includes ultraperformance liquid chromatography-tandem mass spectrometry (UPLC/MS-MS). Particularly suitable immunoassay methods include, for example, enzyme-linked immunosorbent assay (ELISA), Western blot, sandwich immunoassay. Other suitable methods for determining concentrations of steroids and biomarkers include, for example, electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)n, atmospheric pressure photoionization mass spectrometry (APPI-MS), APPI-MS/

MS, and APPI-(MS)n, quadrupole mass spectrometry, fourier transform mass spectrometry (FTMS), and ion trap mass spectrometry.

In one particularly suitable embodiment, the present disclosure is directed to a method for identifying a pregnant female who is susceptible to spontaneous preterm delivery. The method includes obtaining a sample from the pregnant female; determining a concentration of deoxycorticosterone (DOC); determining a concentration of 16α-hydroxyprogesterone (16αOHP); calculating a ratio of DOC/16αOHP; and identifying the pregnant female as being susceptible to spontaneous preterm delivery when the DOC/16αOHP ratio in the sample is reduced below a threshold value.

The sample can be obtained at gestational times ranging from about 8 weeks to about 41 weeks. In one embodiment, the sample is obtained at a gestational age ranging from about 8 weeks to about 24 weeks. In another embodiment, the sample is obtained at a gestational age ranging from about 25 weeks to about 35 weeks. In one embodiment, the sample is obtained at less than 34 weeks gestation. In another embodiment, the sample is obtained at less than 32 weeks gestation. In another embodiment, the sample is obtained at less than 30 weeks.

In one embodiment, the sample is obtained from the pregnant female in the first trimester. In one embodiment, the sample is obtained from the pregnant female in the second trimester. In one embodiment, the sample is obtained from the pregnant female in the third trimester.

Suitable samples include a plasma sample, a serum sample, a whole blood sample, and a urine sample. Plasma samples and urine samples are particularly suitable.

The concentration of DOC is determined using an assay that contacts the sample with an antibody that specifically binds to DOC.

The concentration of 16αOHP is determined using an assay that contacts the sample with an antibody that specifically binds to 16αOHP.

Suitable assays for contacting antibodies that specifically bind to DOC and for contacting antibodies that specifically bind to 16αOHP include enzyme immunoassay (EIA), enzyme-linked immunosorbent assay (ELISA), and radioimmunoassay (RIA).

The method can further include analyzing at least one pregnancy risk factor. Suitable risk factors include, for example, age, race, medication exposure (e.g., administration or previous administration to (e.g., 17 hydroxyprogesterone, progesterone), prior pregnancy, history of previous low birth weight or preterm delivery, multiple 2nd trimester spontaneous abortion, prior first trimester induced abortion, preeclampsia, familial and intergenerational factors, history of infertility, nulliparity, placental abnormalities, cervical and uterine anomalies, gestational bleeding, intrauterine growth restriction, in utero diethylstilbestrol exposure, multiple gestations, infant sex, short stature, low prepregnancy weight/low body mass index, diabetes, hypertension, hypothyroidism, asthma, education level, tobacco use, and urogenital infections.

The method can further include determining a concentration of at least one additional biomarker as described herein.

In another particularly suitable embodiment, the present disclosure is directed to a method for identifying a pregnant female who is susceptible to spontaneous preterm delivery. The method includes obtaining a sample from the pregnant female; determining a concentration of deoxycorticosterone (DOC); determining a concentration of 11-deoxycortisol; calculating a ratio of DOC/11-deoxycortisol; and identifying the pregnant female as being susceptible to spontaneous preterm delivery when the DOC/11-deoxycortisol ratio in the sample is reduced below a threshold value.

The sample can be obtained at gestational times ranging from about 8 weeks to about 41 weeks. In one embodiment, the sample is obtained at a gestational age ranging from about 8 weeks to about 24 weeks. In another embodiment, the sample is obtained at a gestational age ranging from about 25 weeks to about 35 weeks. In one embodiment, the sample is obtained at less than 34 weeks gestation. In another embodiment, the sample is obtained at less than 32 weeks. In another embodiment, the sample is obtained at less than 30 weeks.

In one embodiment, the sample is obtained from the pregnant female in the first trimester. In one embodiment, the sample is obtained from the pregnant female in the second trimester. In one embodiment, the sample is obtained from the pregnant female in the third trimester.

Suitable samples include a plasma sample, a serum sample, a whole blood sample, a salivary sample, and a urine sample. Plasma samples and urine samples are particularly suitable.

The concentration of DOC is determined using an assay that contacts the sample with an antibody that specifically binds to DOC.

The concentration of 16αOHP is determined using an assay that contacts the sample with an antibody that specifically binds to 16αOHP.

Suitable assays for contacting antibodies that specifically bind to DOC and for contacting antibodies that specifically bind to 16αOHP include enzyme immunoassay (EIA), enzyme-linked immunosorbent assay (ELISA), and radioimmunoassay (RIA).

The method can further include analyzing at least one pregnancy risk factor. Suitable risk factors include, for example, age, prior pregnancy, history of previous low birth weight or preterm delivery, multiple 2nd trimester spontaneous abortion, prior first trimester induced abortion, familial and intergenerational factors, history of infertility, nulliparity, placental abnormalities, cervical and uterine anomalies, gestational bleeding, intrauterine growth restriction, in utero diethylstilbestrol exposure, multiple gestations, infant sex, short stature, low prepregnancy weight/low body mass index, diabetes, hypertension, hypothyroidism, asthma, education level, tobacco use, and urogenital infections.

The method can further include determining a concentration of at least one additional biomarker as described herein.

In another particularly suitable embodiment, the present disclosure is directed to a method for identifying a pregnant female who is susceptible to spontaneous preterm delivery. The method includes obtaining a sample from the pregnant female; determining a concentration of deoxycorticosterone (DOC); determining a concentration of 16αOHP; determining a concentration of 6βOHP; calculating a ratio of DOC/16αOHP and 6βOHP; and identifying the pregnant female as being susceptible to spontaneous preterm delivery when the DOC/16αOHP and 6βOHP ratio in the sample is reduced below a threshold value.

The sample can be obtained at gestational times ranging from about 8 weeks to about 41 weeks. In one embodiment, the sample is obtained at a gestational age ranging from about 8 weeks to about 24 weeks. In another embodiment, the sample is obtained at a gestational age ranging from about 25 weeks to about 35 weeks. In one embodiment, the sample is obtained at less than 34 weeks gestation. In another embodiment, the sample is obtained at less than 32 weeks. In another embodiment, the sample is obtained at less than 30 weeks.

In one embodiment, the sample is obtained from the pregnant female in the first trimester. In one embodiment, the sample is obtained from the pregnant female in the second trimester. In one embodiment, the sample is obtained from the pregnant female in the third trimester.

Suitable samples include a plasma sample, a serum sample, a whole blood sample, a salivary sample, and a urine sample. Plasma samples and urine samples are particularly suitable.

The method can further include analyzing at least one pregnancy risk factor. Suitable risk factors include, for example, age, prior pregnancy, history of previous low birth weight or preterm delivery, multiple 2nd trimester spontaneous abortion, prior first trimester induced abortion, familial and intergenerational factors, history of infertility, nulliparity, placental abnormalities, cervical and uterine anomalies, gestational bleeding, intrauterine growth restriction, in utero diethylstilbestrol exposure, multiple gestations, infant sex, short stature, low prepregnancy weight/low body mass index, diabetes, hypertension, hypothyroidism, asthma, education level, tobacco use, and urogenital infections.

The method can further include determining a concentration of at least one additional biomarker as described herein.

II. Methods of Treatment

In another embodiment, the present disclosure is directed to treating a pregnant female upon identifying the female as being susceptible to spontaneous preterm delivery. Generally, the disclosure provides for a method for treating a pregnant female susceptible to spontaneous preterm delivery with an agent that can antagonize the glucocorticoid pathway. Exemplary compounds include progesterone, 17α-hydroxyprogesterone caproate (HPC), monohydrogenated HPC (HPC-OH), atosiban, nifedipine, terbutaline, eplerenone, other mineralocorticoid specific antagonists, modulators of cytochrome P450 function (e.g., CYP2D6, CYP2C9, CYP3A4), and derivatives thereof. The method comprises determining a ratio of at least two steroids in the pregnant female using the detection methods described above. Particularly, the methods include obtaining a sample from the pregnant female; detecting a concentration of a first steroid in the sample; detecting a concentration of at least a second steroid in the sample, wherein the second steroid is different from the first steroid; and detecting a ratio of the first steroid to the at least second steroid. Further, if the ratio of the first steroid to the at least second steroid is less than 0.2, then the methods provide for administering an effective amount of the compound (i.e., 17α-hydroxyprogesterone caproate (HPC), HPC-OH, atosiban, nifedipine, terbutaline, eplerenone, and derivatives thereof).

In an embodiment, the treatment methods described herein provide for a method of treating a pregnant female with one or more compounds selected progesterone, 17α-hydroxyprogesterone caproate (HPC), monohydrogenated HPC (HPC-OH), atosiban, nifedipine, terbutaline, eplerenone, and derivatives thereof.

In an embodiment, the steroids for use in the treatment methods include those described above. Particularly suitable steroids include, for example, deoxycorticosterone, corticorterone, 18-hydroxycortiosterone, aldosterone, deoxycortisol, cortisol, and combinations thereof. Suitable steroids can also be selected from progesterone, 16α-hydroxyprogesterone, 6β-hydroxyprogesterone, 6α-hydroxyprogesterone, 17-hydroxyprogesterone, 11-deoxycortisol, cortisol, 11-deoxycorticosterone, 17-deoxycortisol, androstenedione, testosterone, estradiol, 20α-dihydroprogesterone, 17α,20α-dihydroxyprogesterone, isopregnanolone, and combinations thereof. By way of example, in some embodiments, the first steroid is deoxycorticosterone (DOC) and the second steroid is 16α-hydroxyprogesterone (16αOHP). In other embodiments, the first steroid is deoxycorticosterone (DOC) and the second steroid is 11-deoxycortisol.

The treatment methods can further include determining a change in a concentration of at least one additional biomarker selected from insulin-like growth factor binding protein 4, sex-hormone binding globulin (SHBG), lipopolysaccharide-binding protein (LBP), lipopolysaccharide-binding protein (LBP) precursor, prothrombin (THRB), complement component C5 (C5 or CO5), plasminogen (PLMN), complement component C8 gamma chain (C8G or CO8G), Complement factor B, Ectonucleotide pyrophosphatase/phosphodiesterase family member 2, Gelsolin, N-acetylmuramoyl-L-alanine amidase, N-acetylmuramoyl-L-alanine amidase precursor, Hyaluronan-binding protein 2, BPI fold-containing family B member 1, complement component C8 alpha chain, apolipoprotein A-II, Ectonucleotide pyrophosphatase/phosphodiesterase family member 2, profiling-1, pro-neuropeptide Y, complement component C8 beta chain, coagulation factor XIII B chain, N-acetylmuramoyl-L-alanine amidase, inter-alpha-trypsin inhibitor heavy chain H4, inter-alpha-trypsin inhibitor heavy chain H3 preproprotein, leucyl-cystinyl aminopeptidase, alpha-2-HS-glycoprotein, 5'-AMP-activated protein kinase subunit gamma-3, afamin precursor, alpha-1-antichymotrypsin precursor, alpha-1B-glycoprotein precursor, alpha-2-antiplasmin isoform a precursor, alpha-2-HS-glycoprotein preproprotein, alpha-2-HS-macroglobulin precursor, angiotensinogen preproprotein, antithrombin-III precursor, apolipoprotein A-II preproprotein, apolipoprotein A-IV precursor, apolipoprotein B-100 precursor, apolipoprotein C-I precursor, apolipoprotein C-II precursor, apolipoprotein C-III precursor, apolipoprotein E precursor, ATP-binding cassette sub-family D member 4, ATP-binding cassette sub-family F member 3, beta-2-glycoprotein 1 precursor, beta-Ala-His dipeptidase precursor, biotinidase precursor, carboxypeptidase B2 preproprotein, carboxypeptidase N catalytic chain precursor, carboxypeptidase N subunit 2 precursor, catalase, ceruloplasmin precursor, cholinesterase precursor, clusterin preproprotein, coagulation factor IX preproprotein, coagulation factor VII isoform a, coagulation factor VII isoform a preproprotein, coagulation factor X preproprotein, coagulation factor XIII B chain, coiled-coil domain-containing protein 13, complement C1q subcomponent subunit A precursor, complement C1q subcomponent subunit B precursor, complement C1q subcomponent subunit C precursor, complement C1r subcomponent precursor, complement C1s subcomponent precursor, complement C2 isoform 3, complement C3 precursor, complement C4-A isoform 1, complement C5 preproprotein, component C6 precursor, component C7 precursor, component C8 alpha chain precursor, complement component C9 precursor, complement factor B preproprotein, complement factor H isoform a precursor, complement factor H isoform b precursor, complement factor H H-related protein 1 precursor, complement factor I preproprotein, conserved oligomeric Golgi complex subunit 6 isoform, corticosteroid-binding globulin precursor, C-reactive protein precursor, dopamine beta-hydroxylase precursor, double-stranded RNA-specific editase B2, dual oxidase 2 precursor, FERM domain-containing protein 8, fetuin-B precursor, ficolin-3 isoform 1 precursor, gastric intrinsic factor precursor, gelsolin isoform d, glutathione peroxidase 3 precursor, hemopexin precursor, heparin cofactor 2 precursor, hepatocyte cell adhesion molecule precursor, hepatocyte growth factor activator preproprotein, histidine-rich glycoprotein precursor, hyaluronan-binding protein 2 isoform 1 preproprotein, inactive caspase-12 insulin-degrading enzyme isoform 1, insulin-like growth factor-binding protein complex acid labile subunit isoform 2 precursor, inter-alpha-trypsin inhibitor heavy chain H1 isoform a precursor, inter-alpha-trypsin inhibitor heavy chain H2 precursor, inter-alpha-trypsin inhibitor heavy chain H4 isoform 1 precursor, kallistatin precursor, kininogen-1 isoform 2 precursor, leucine-rich alpha-2-glycoprotein precursor, lumican precursor, m7GpppX diphosphatase, matrix metalloproteinase-19 isoform 1 preproprotein, MBT domain-containing protein 1, monocyte differentiation antigen CD14 precursor, pappalysin-1 preproprotein, phosphatidylinositol-glycan-specific phospholipase D precursor, pigment epithelium-derived factor precursor, plasma kallikrein preproprotein, plasma protease C1 inhibitor precursor, plasminogen isoform 1 precursor, platelet basic protein preproprotein, platelet glycoprotein V precursor, pregnancy zone protein precursor, pregnancy-specific beta-1-glycoprotein 5, pregnancy-specific beta-1-glycoprotein 5 precursor, pregnancy-specific beta-1-glycoprotein 6, pregnancy-specific beta-1-glycoprotein 6 precursor, pregnancy-specific beta-1-glycoprotein 7, pregnancy-specific beta-1-glycoprotein 8, pregnancy-specific beta-1-glycoprotein 9, pregnancy-specific beta-1-glycoprotein 11, pregnancy-specific beta-1-glycoprotein 2, pregnancy-specific beta-1-glycoprotein 3, pregnancy-specific beta-1-glycoprotein 4, progesterone-induced-blocking factor 1, protein AMBP preproprotein, protein CBFA2T2 isoform MTGR1b, protein FAM98C, protein NLRC3, protein Z-dependent protease inhibitor precursor, prothrombin preproprotein, putative hydroxypyruvate isomerase isoform 1, ras-like protein family member 10A precursor, ras-related GTP-binding protein A, retinol-binding protein 4 precursor, sex hormone-binding globulin isoform 1 precursor, sex hormone-binding globulin isoform 4 precursor, signal transducer and activator of transcription 2, spectrin beta chain non-erythrocytic 1, stabilin-1 precursor, succinate semialdehyde dehydrogenase mitochondrial, tetranectin precursor, THAP domain-containing protein 6, thyroxine-binding globulin precursor, tripartite motif-containing protein 5, vitamin D-binding protein isoform 1 precursor, vitronectin precursor, zinc finger protein 142, attractin isoform 2 preproprotein, transforming growth factor-beta-induced protein ig-h3 precursor, transthyretin precursor, uncharacterized protein C3orf20, beta-2-microglobulin precursor, bone marrow proteoglycan isoform 1 preproprotein, chorionic gonadotropin beta polypeptide 8 precursor, chorionic somatomammotropin hormone 2 isoform 2 precursor, macrophage colony-stimulating factor 1 receptor precursor, zinc-alpha-2-glycoprotein precursor, PAN-PSG, complement component C6 precursor, EGF-containing fibulin-like extracellular matrix protein 1, and disintegrin and metalloproteinase domain-containing protein 12. Ratios can be obtained by pairing these biomarkers with the steroids described above. Methods of measuring concentrations of these biomarkers in pregnant females are described Saade et al., Am J of Obstetrics & Gynecology, May 2016 633e1-633e24, which is incorporated by reference to the extent it is consistent herewith.

In yet another embodiment, the method can further include determining a change in a concentration of at least one calmodulin 1 (CALM1), calmodulin 2 (CALM2), and calmodulin 3 (CALM3) prior to administering or after administration of the compound. A decrease in the concentration of one or more of CALM1, CALM2, and CALM3 after administration of the compound indicates the pregnant female is effectively being treated. Additionally, an increase in the concentration of one or more of CALM1, CALM2, and CALM3 after administration of the compound indicates a need to continue administration of the compound to the pregnant female.

The method can further include determining a change in nucleic acids of the pregnant female. More particularly, nucleic acids for combinatorial use in the methods of the present disclosure can include nucleic acid primers and/or probes that bind with specific nucleic acid sequences as well as the nucleic acids that are increased or decreased in concentration in pregnant females that are susceptible to preterm delivery. In suitable embodiments, the nucleic acids can include cell free plasma (CFP) RNA such as disclosed in U.S. Publication No. 2015/0376709 to Dong et al. (Sep. 11, 2015). In other embodiments, the nucleic acids can include cell free fetal DNA ("fetal fraction").

The sample can be obtained at gestational times ranging from about 8 weeks to about 41 weeks. In one embodiment, the sample is obtained at a gestational age ranging from about 8 weeks to about 24 weeks. In another embodiment, the sample is obtained at a gestational age ranging from about 25 weeks to about 35 weeks. In one embodiment, the sample is obtained at less than 34 weeks gestation. In another embodiment, the sample is obtained at less than 32 weeks gestation. In another embodiment, the sample is obtained at less than 30 weeks.

In one embodiment, the sample is obtained from the pregnant female in the first trimester, generally considered from the date of the last menstrual period to 13 weeks. In one embodiment, the sample is obtained from the pregnant female in the second trimester, generally considered from about the 14th week to about the 27th week. In one embodiment, the sample is obtained from the pregnant female in the third trimester, generally considered from about the 28th week to about the 42nd week.

Suitable samples include a plasma sample, a serum sample, a whole blood sample, salivary sample, and a urine sample. Plasma samples and urine samples are particularly suitable.

The methods can further include analyzing at least one pregnancy risk factor. Suitable risk factors include, for example, age, prior pregnancy, history of previous low birth weight or preterm delivery, multiple 2nd trimester spontaneous abortion, prior first trimester induced abortion, preeclampsia, familial and intergenerational factors, history of infertility, environmental factors, nulliparity, placental abnormalities, cervical and uterine anomalies, gestational bleeding, intrauterine growth restriction, in utero diethylstilbestrol exposure, multiple gestations, infant sex, short stature, low prepregnancy weight/low body mass index, diabetes, hypertension, hypothyroidism, asthma, education level, tobacco use, and urogenital infections.

Suitable methods for determining concentrations of steroids and biomarkers can be, for example, immunoassays, chromatography, mass spectrometry, amplification, microarray analysis, and combinations thereof. A particularly suitable chromatography-mass spectrometry method includes ultraperformance liquid chromatography-tandem mass spectrometry (UPLC/MS-MS). Particularly suitable immunoassay methods include, for example, enzyme-linked immunosorbent assay (ELISA), Western blot, sandwich immunoassay. Other suitable methods for determining concentrations of steroids and biomarkers include, for example, electrospray ionization mass spectrometry (ESI-MS), ESI- MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)n, atmospheric pressure photoionization mass spectrometry (APPI-MS), APPI-MS/MS, and APPI-(MS)n, quadrupole mass spectrometry, fourier transform mass spectrometry (FTMS), and ion trap mass spectrometry.

The treatment methods include administering an effective amount of one or more of progesterone, 17α-hydroxyprogesterone caproate (HPC), monohydrogenated HPC (HPC-OH), atosiban, nifedipine, terbutaline, eplerenone, and derivatives thereof to the female patient when the ratio of the first steroid to the at least second steroid is less than 0.2, suitably, less than 0.15, and more suitably, less than 0.1. In another embodiment, one or more of progesterone, 17α-hydroxyprogesterone caproate (HPC), monohydrogenated HPC (HPC-OH), atosiban, nifedipine, terbutaline, eplerenone, and derivatives thereof is administered to the female patient when the ratio of the first steroid to the at least second steroid is from 0.1 to 0.2, including from 0.15 to 0.2.

In particularly suitable embodiments, one or more of 17α-hydroxyprogesterone caproate (HPC), monohydrogenated HPC (HPC-OH), atosiban, nifedipine, terbutaline, eplerenone, and derivatives thereof is administered to the female patient after 10 weeks of gestation, suitably, after 12 weeks of gestation and even more suitably, at or after 16 weeks gestation.

Suitable dosages of 17α-hydroxyprogesterone caproate (HPC), monohydrogenated HPC (HPC-OH), atosiban, nifedipine, terbutaline, eplerenone, and/or derivatives thereof may be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

Suitable amounts of one or more of 17α-hydroxyprogesterone caproate (HPC), monohydrogenated HPC (HPC-OH), atosiban, nifedipine, terbutaline, eplerenone, and/or derivatives thereof for use in the dosage forms of the present disclosure will depend upon many factors including, for example, age and weight of an pregnant female, specific compound(s) to be used, nature of a composition, whether the composition is intended for direct administration or is a concentrate, and combinations thereof.

The methods can further include analyzing administering or modifying a life factor selected from exercise regimen, dietary regimen, sleep patterns, and smoking cessation.

Suitable female subjects include, but are not limited to, a human female, a livestock female animal, a companion female animal, a lab female animal, and a zoological female animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In another embodiment, the animal is a laboratory animal. Non-limiting examples of a laboratory animal may include rodents, canines, felines, and non-human primates. In certain embodiments, the animal is a rodent. In a further embodiment, the subject is human.

The disclosure will be more fully understood upon consideration of the following non-limiting Examples.

EXAMPLES

Example 1

In this Example, the relationship between CYP3A-mediated progesterone metabolites (16α-hydroxyprogesterone [16αOHP], 6β-hydroxyprogesterone [6βOHP]) and major endogenous steroids for the timing of preterm birth.

Methods: Analysis was performed on prospectively collected specimens from a cohort of women enrolled in a pregnancy registry who delivered term and preterm (<36 weeks gestation). Plasma samples were divided into 2 epochs for analysis: epoch 1 (second trimester) and epoch 2 (third trimester, within 2 weeks of delivery). A targeted metabolomics approach was used to quantify up to 15 endogenous steroids using ultraperformance liquid chromatography-tandem mass spectrometry (UPLC/MS-MS) analysis: progesterone, 16α-hydroxyprogesterone, 6β-hydroxyprogesterone, 6α-hydroxyprogesterone, 17-hydroxyprogesterone, 11-deoxycortisol, cortisol, 11-deoxycorticosterone, 17-deoxycortisol, androstenedione, testosterone, estradiol, 20α-dihydroprogesterone, 17α,20α-dihydroxyprogesterone, and isopregnanolone. Levels of the progesterone metabolites 16αOHP and 6βOHP were compared to gestational age at birth alone and in combination with other endogenous steroid levels using standard statistical methods (ROC curves, two tail t-test, principal component analysis).

| Sample collection Epochs were as follows: | |
|---|---|
| N = 53 total subjects | |
| Epoch 1 | N = 40 |
| Mean | 14.8 weeks gestational age |
| Median | 15.0000 |
| Std. Deviation | 3.44 |
| Range | 16.00 |
| Minimum | 8.00 |
| Maximum | 24.00 |
| Epoch 2 | N-27 |
| Mean | 29.1 weeks gestational age |
| Median | 27.0000 |
| Std. Deviation | 3.2 |
| Range | 10.00 |
| Minimum | 25.00 |
| Maximum | 35.00 |

Figure 2A:
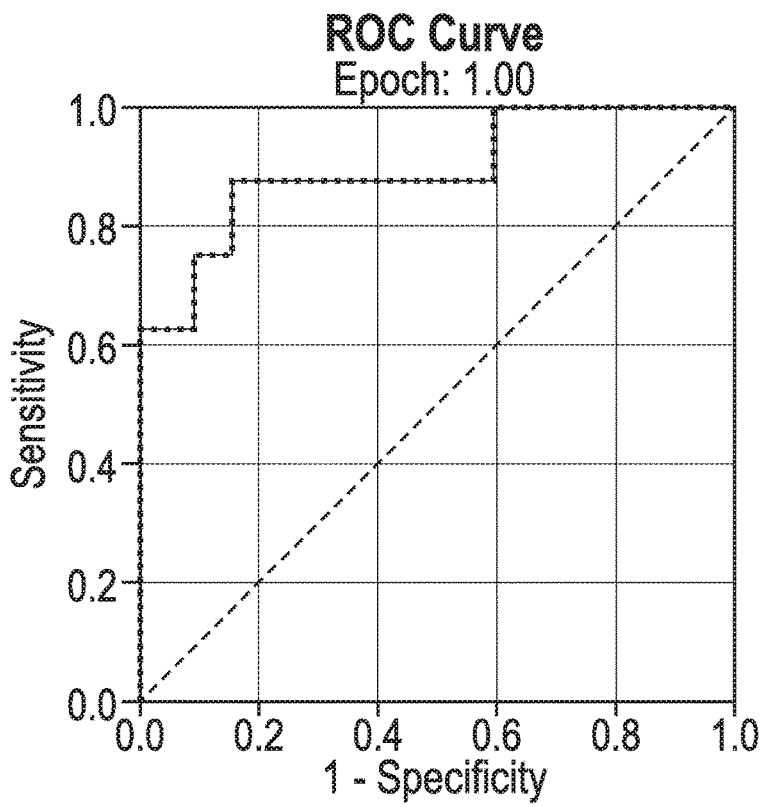
FIGS. 2A and 2B are ROC graphs depicting the DOC/16α-OHP ratio and spontaneous preterm birth (sPTB) at less than 30 weeks in Epoch 1 and Epoch 2.
Figure 2B:
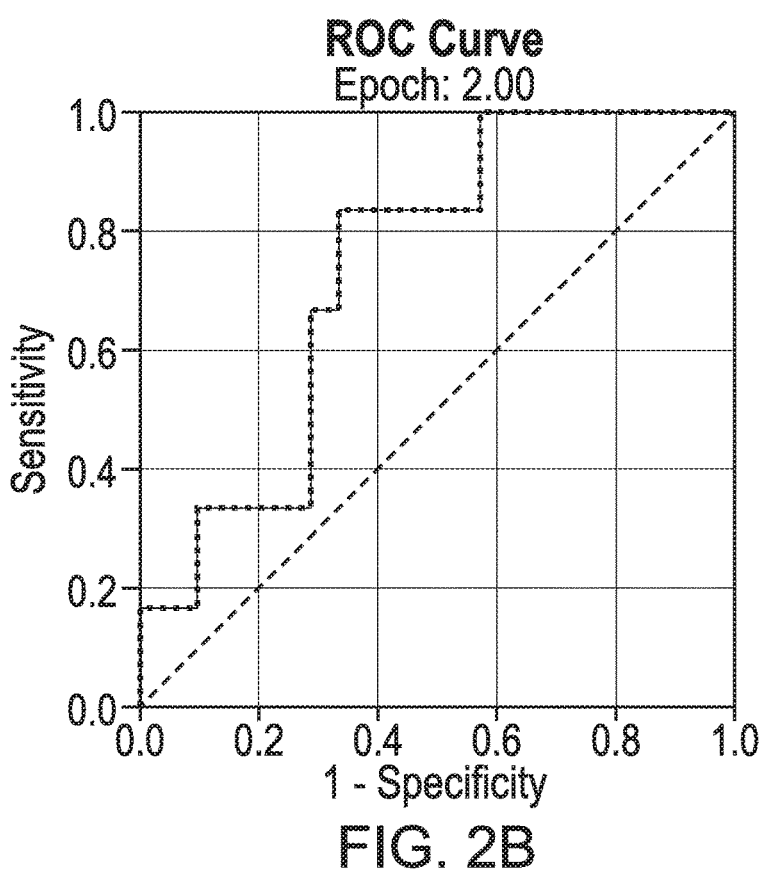

FIG. 2A is a ROC graph depicting the DOC/16α-OHP ratio and spontaneous preterm birth (sPTB) at less than 30 weeks in Epoch 1. AUC 0.895, 95% CI 0.753-1.00 (p=0.001), 88% sensitivity, 84% specificity (threshold≤0.17). FIG. 2B is a ROC graph depicting the DOC/16α-OHP ratio and spontaneous preterm birth (sPTB) at less than 30 weeks in Epoch 2. AUC 0.738, 95% CI 0.537-0.939 (p=0.08), 83% sensitivity, 67% specificity (threshold≤0.25).

Figure 3A:
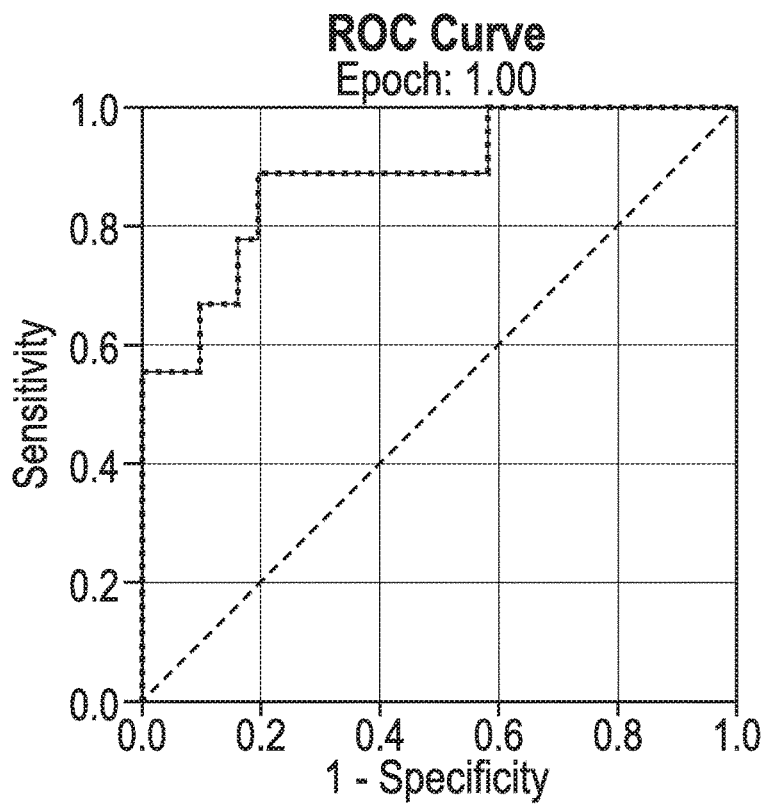
FIGS. 3A and 3B are ROC graphs depicting the DOC/16α-OHP ratio and spontaneous preterm birth (sPTB) at less than 32 weeks in Epoch 1 and Epoch 2.

FIG. 3A is a ROC graph depicting the DOC/16α-OHP ratio and spontaneous preterm birth (sPTB) at less than 32 weeks in Epoch 1. AUC 0.885, 95% CI 0.755-1.00

Figure 3B:
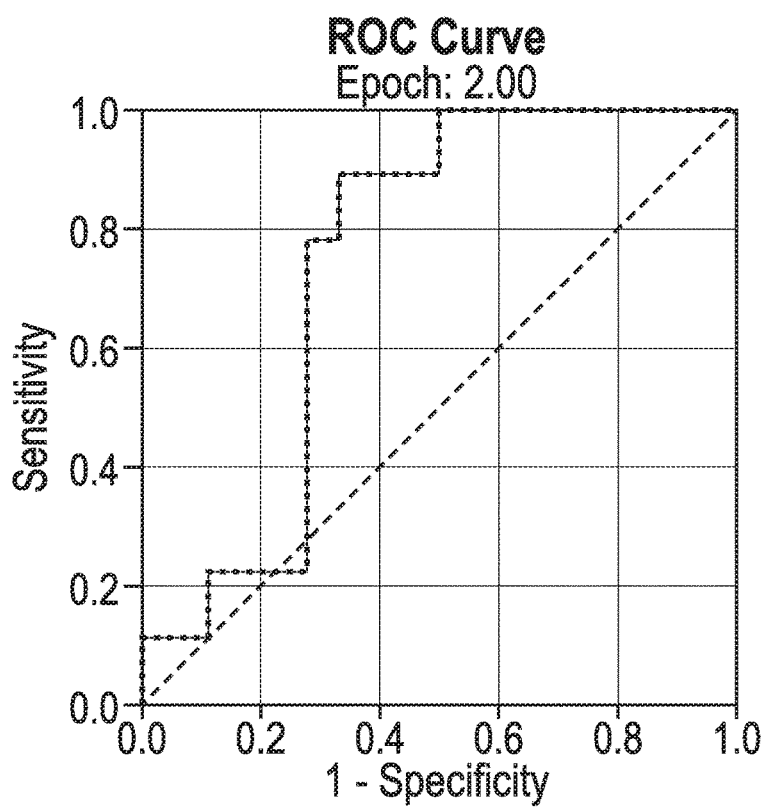

(p=0.001), 89% sensitivity, 81% specificity (threshold≤0.19). FIG. 3B is a ROC graph depicting the DOC/16α-OHP ratio and spontaneous preterm birth (sPTB) at less than 32 weeks in Epoch 2. AUC 0.741, 95% CI 0.553-0.929 (p=0.045), 89% sensitivity, 67% specificity (threshold≤0.29).

Figure 4A:
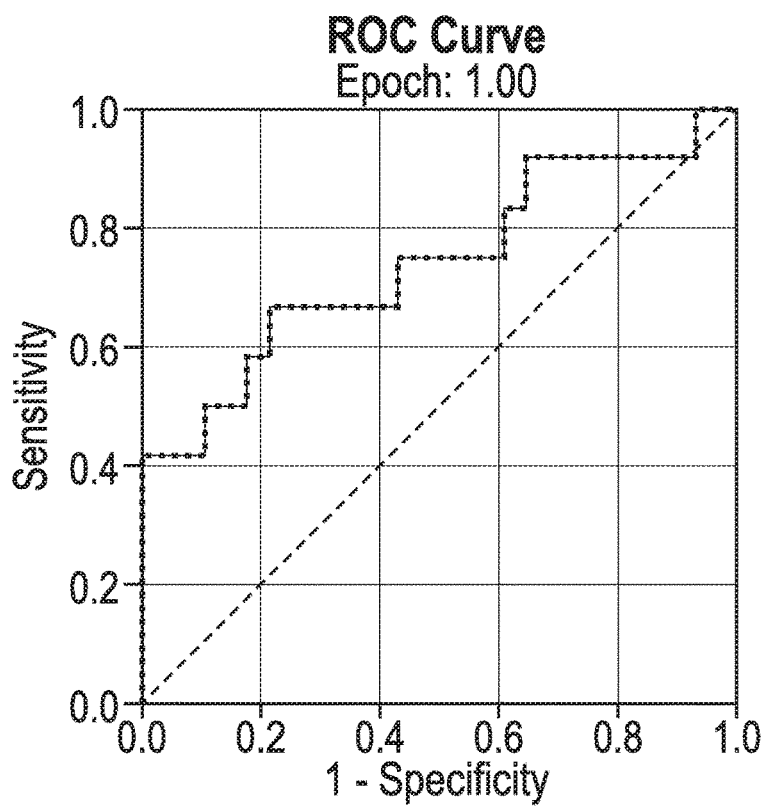
FIGS. 4A and 4B are ROC graphs depicting the DOC/16α-OHP ratio and spontaneous preterm birth (sPTB) at less than 34 weeks in Epoch 1 and Epoch 2.
Figure 4B:
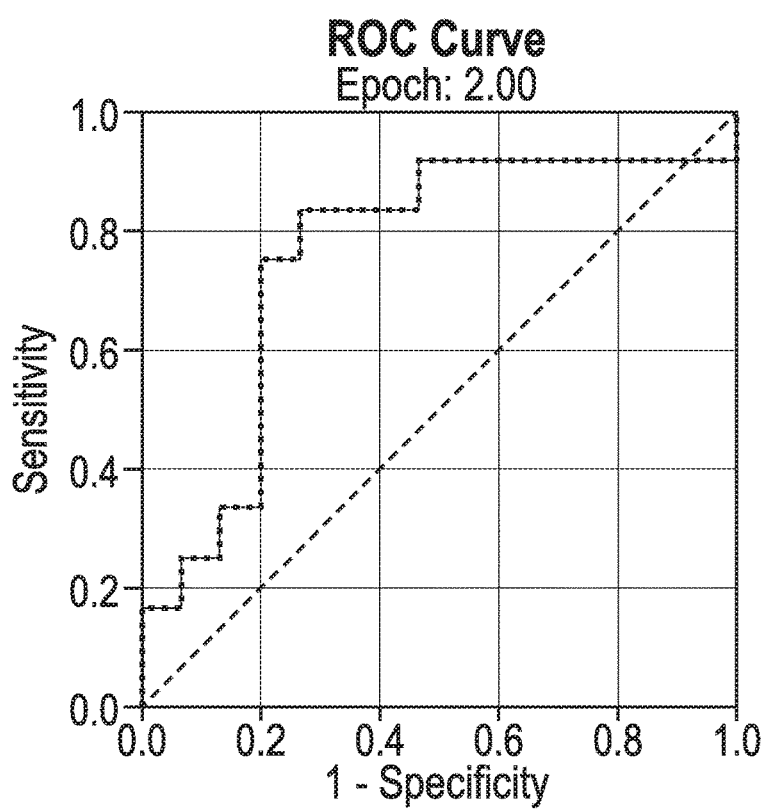

FIG. 4A is a ROC graph depicting the DOC/16α-OHP ratio and spontaneous preterm birth (sPTB) at less than 34 weeks in Epoch 1. AUC 0.741, 95% CI 0.555-0.928 (p=0.08), 67% sensitivity, 79% specificity (threshold≤0.19). FIG. 4B is a ROC graph depicting the DOC/16α-OHP ratio and spontaneous preterm birth (sPTB) at less than 34 weeks in Epoch 2. AUC 0.756, 95% CI 0.557-0.954 (p=0.025), 83% sensitivity, 73% specificity (threshold≤0.29).

Figure 5A:
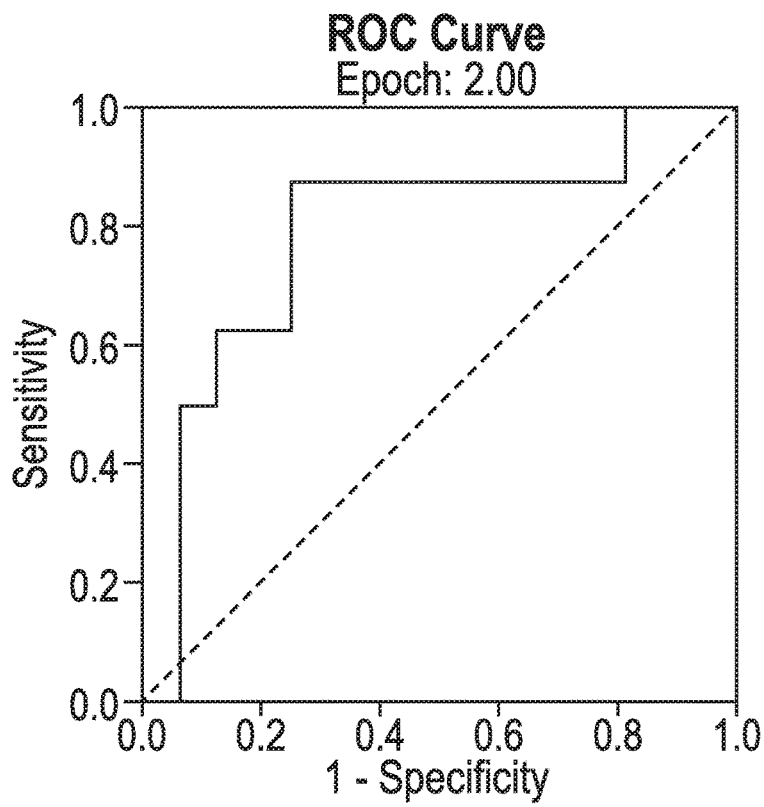
FIGS. 5A and 5B are ROC graphs depicting the DOC/6β-OHP ratio and spontaneous preterm birth (sPTB) at less than 32 weeks and less than 34 weeks in Epoch 2.
Figure 5B:
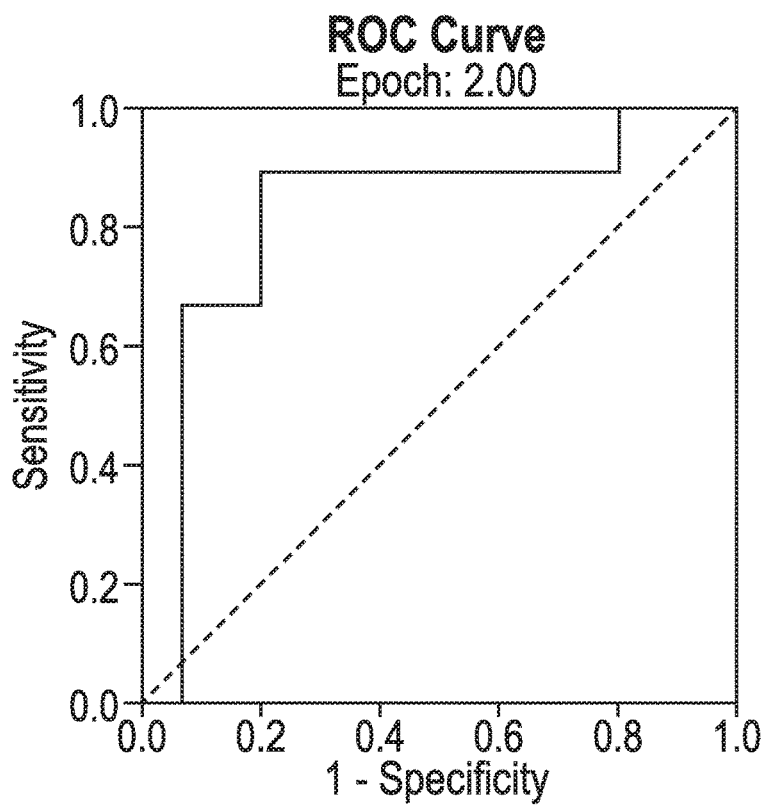

FIG. 5A is a ROC graph depicting the DOC/6β-OHP ratio and spontaneous preterm birth (sPTB) at less than 32 weeks in Epoch 2. AUC 0.789, 95% CI 0.580-0.998 (p=0.02), 88% sensitivity, 75% specificity (threshold≤0.19). FIG. 5B is a ROC graph depicting the DOC/6β-OHP ratio and spontaneous preterm birth (sPTB) at less than 34 weeks in Epoch 2. AUC 0.822, 95% CI 0.628-1.00 (p=0.009), 89% sensitivity, 80% specificity (threshold≤0.19).

Figure 6A:
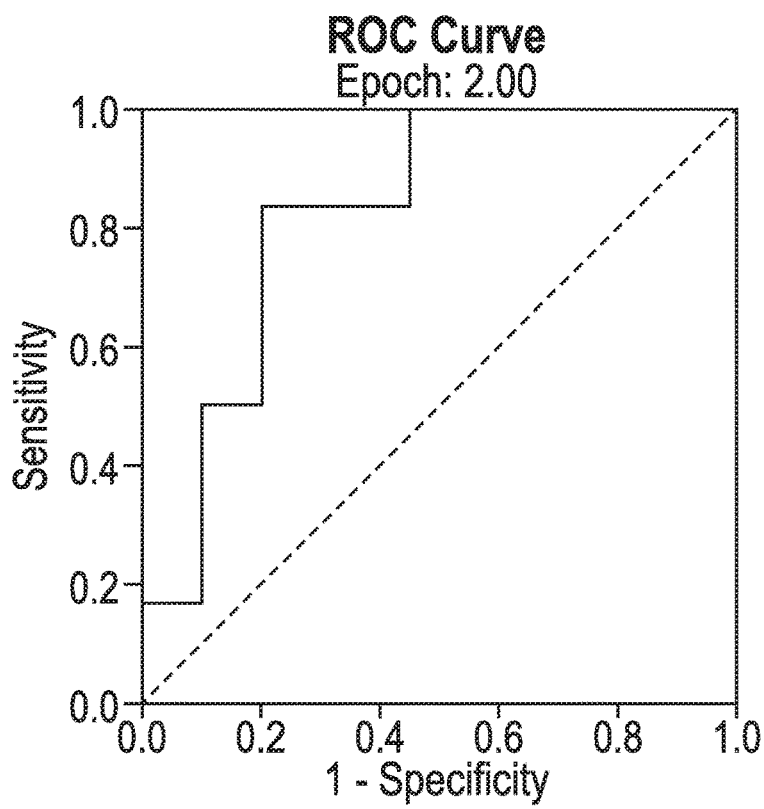
FIGS. 6A and 6B are ROC graphs depicting the DOC/11-deoxycortisol ratio and spontaneous preterm birth (sPTB) at less than 30 weeks and less than 32 weeks in Epoch 2.
Figure 6B:
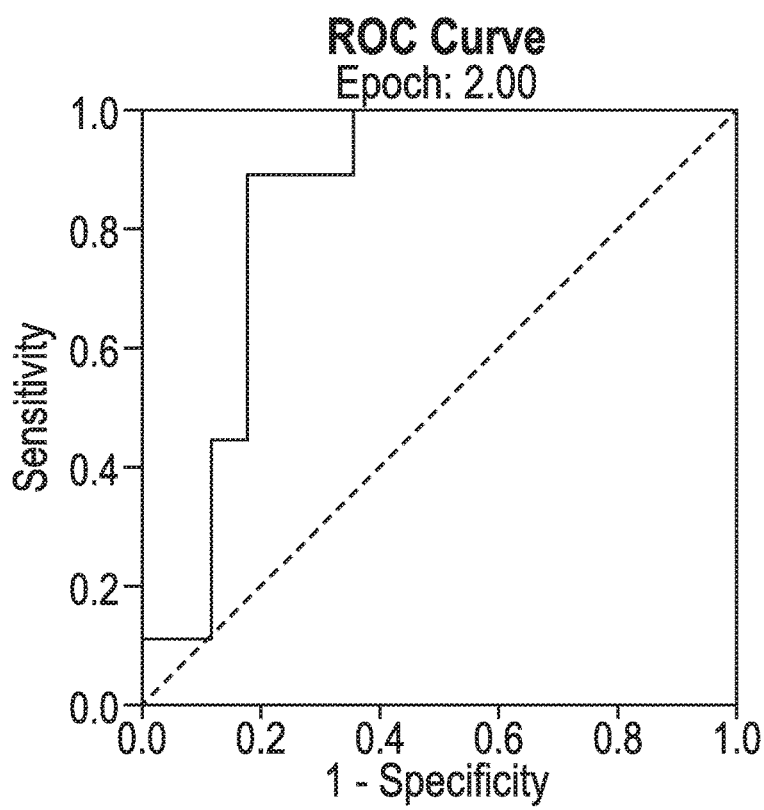

FIG. 6A is a ROC graph depicting the DOC/11-deoxycortisol ratio and spontaneous preterm birth (sPTB) at less than 30 weeks in Epoch 2. AUC 0.825, 95% CI 0.658-0.992 (p=0.018), 83% sensitivity, 80% specificity (threshold≤0.16). FIG. 6B is a ROC graph depicting the DOC/11-deoxycortisol ratio and spontaneous preterm birth (sPTB) at less than 32 weeks in Epoch 2. AUC 0.843, 95% CI 0.688-0.999 (p=0.005), 89% sensitivity, 82% specificity (threshold≤0.18).

Figure 7A:
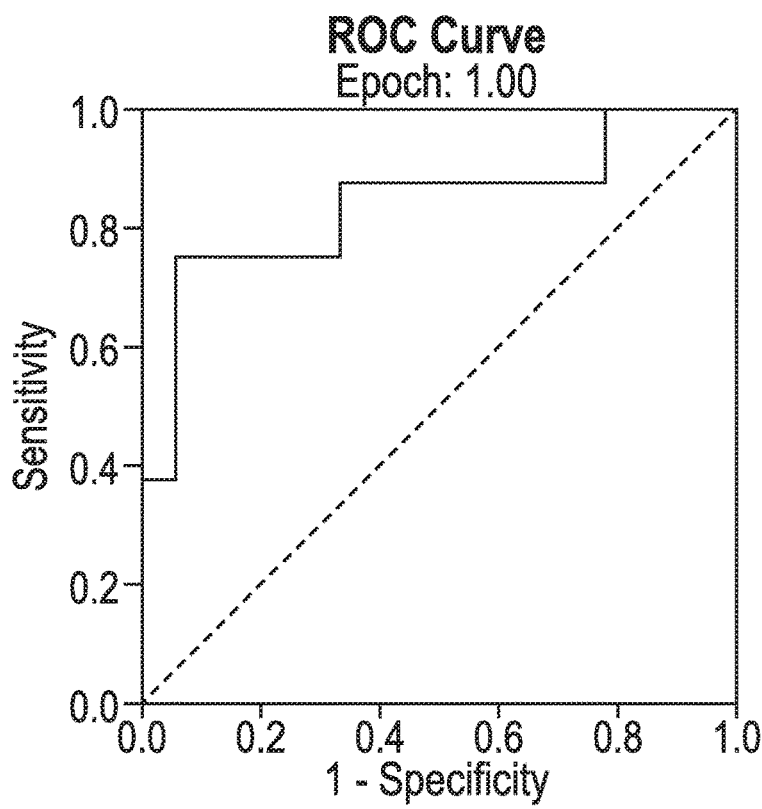
FIGS. 7A and 7B are ROC graphs depicting the DOC/(16α-OHP+6β-OHP) and spontaneous preterm birth (sPTB) at less than 30 weeks in Epoch 1 and Epoch 2.
Figure 7B:
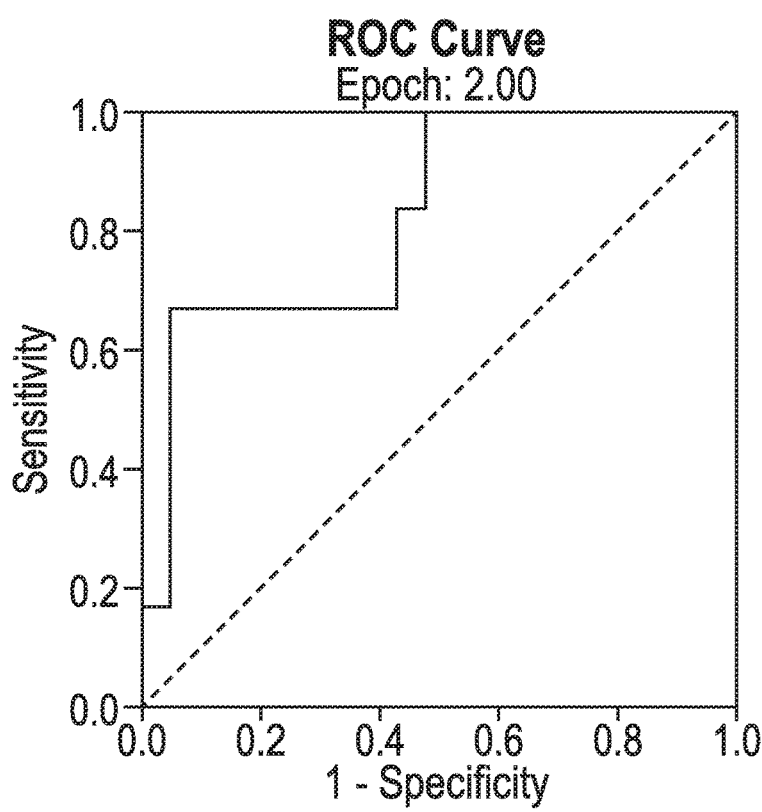

FIG. 7A is a ROC graph depicting the DOC/(16α-OHP+6β-OHP) and spontaneous preterm birth (sPTB) at less than 30 weeks in Epoch 1. AUC 0.840, 95% CI 0.648-1.00 (p=0.006), 75% sensitivity, 94% specificity (threshold≤0.05). FIG. 7B is a ROC graph depicting the DOC/(16α-OHP+6β-OHP) and spontaneous preterm birth (sPTB) at less than 30 weeks in Epoch 2. AUC 0.825, 95% CI 0.638-1.00 (p=0.017), 67% sensitivity, 95% specificity (threshold≤0.058).

Figure 8A:
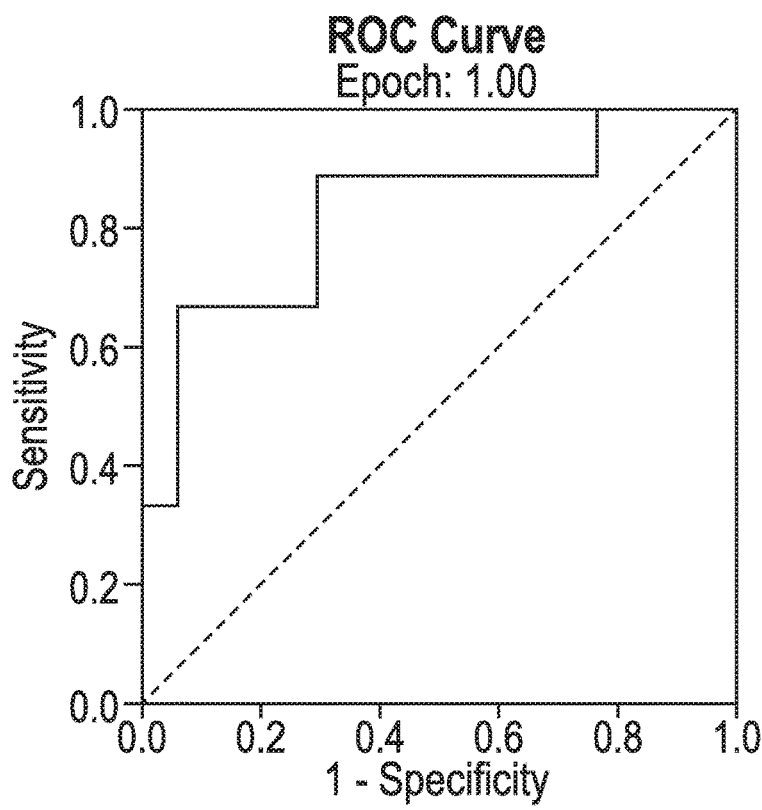
FIGS. 8A and 8B are ROC graphs depicting the DOC/(16α-OHP+6β-OHP) and spontaneous preterm birth (sPTB) at less than 32 weeks in Epoch 1 and Epoch 2.
Figure 8B:
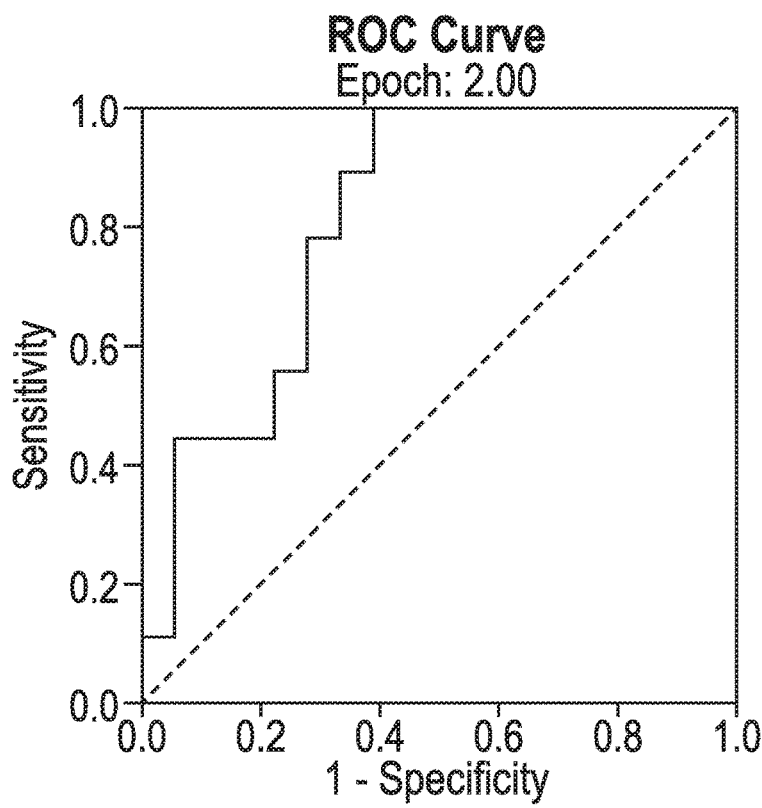

FIG. 8A is a ROC graph depicting the DOC/(16α-OHP+6β-OHP) and spontaneous preterm birth (sPTB) at less than 32 weeks in Epoch 1. AUC 0.830, 95% CI 0.651-1.00 (p=0.006), 89% sensitivity, 71% specificity (threshold≤0.12). FIG. 8B is a ROC graph depicting the DOC/(16α-OHP+6β-OHP) and spontaneous preterm birth (sPTB) at less than 32 weeks in Epoch 2. AUC 0.815, 95% CI 0.656-0.974 (p=0.009), 100% sensitivity, 61% specificity (threshold≤0.13).

Figure 9A:
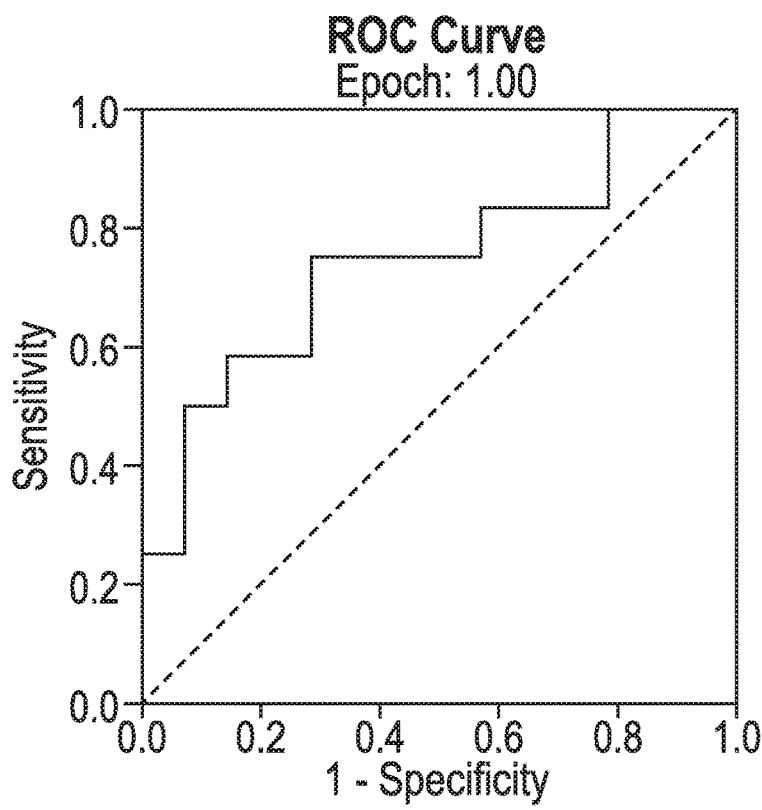
FIGS. 9A and 9B are ROC graphs depicting the DOC/(16α-OHP+6β-OHP) and spontaneous preterm birth (sPTB) at less than 34 weeks in Epoch 1 and Epoch 2.
Figure 9B:
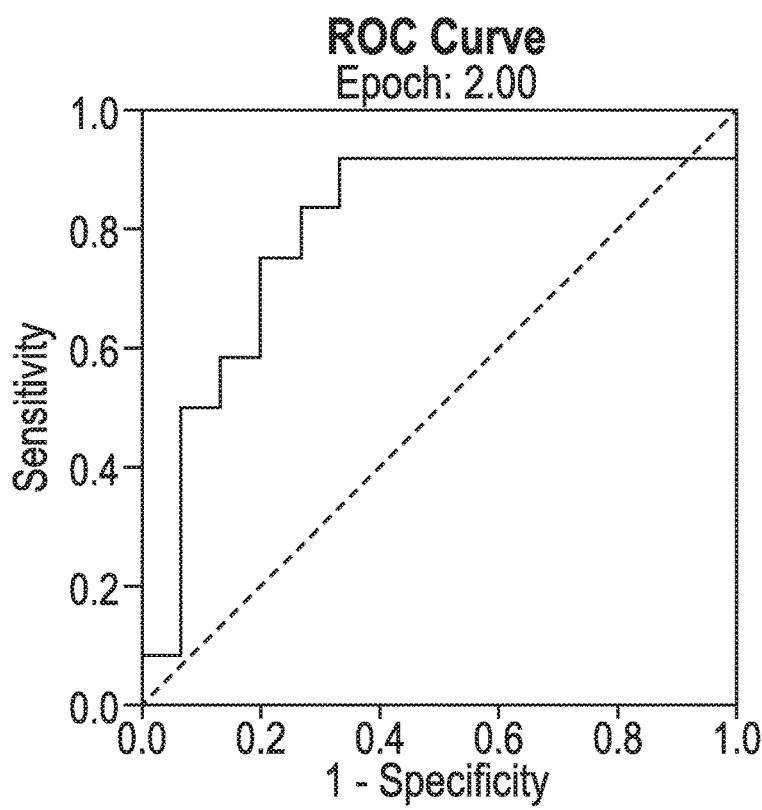

FIG. 9A is a ROC graph depicting the DOC/(16α-OHP+6β-OHP) and spontaneous preterm birth (sPTB) at less than 34 weeks in Epoch 1. AUC 0.744, 95% CI 0.547-0.941 (p=0.035), 75% sensitivity, 71% specificity (threshold≤0.12). FIG. 9B is a ROC graph depicting the DOC/(16α-OHP+6β-OHP) and spontaneous preterm birth (sPTB) at less than 34 weeks in Epoch 2. AUC 0.794, 95% CI 0.606-0.983 (p=0.01), 92% sensitivity, 67% specificity (threshold≤0.13).

Observations: Based on analyzing concentrations of a broad range of endogenous steroids, the most significant results were related to derivatives of progesterone along the glucocorticoid/mineralocorticoid pathways.

The pairing of cortexone with either 16αOHP or cortexolone obtained from samples from subjects in the second or third trimesters was the most promising indicator of spontaneous preterm delivery (using cutoffs of less than 32 or less than 30 weeks). ROC values using the ratio of these molecules were high, indicating risk of spontaneous preterm delivery. Notably, none of the steroids alone were indicative of spontaneous preterm birth. Comparison of the sensitivity and specificity values for these compounds is equal to or above the performance of currently available screening tools for spontaneous very preterm birth (<32 weeks) risk.

The present disclosure improves upon the current technologies in several ways: (1) the sensitivity/specificity of the algorithm is equal to or better than the existing diagnostic tools; (2) the algorithm was able to predict the occurrence of spontaneous preterm delivery in the early second trimester, a complete month before the earliest of the current serologic testing options; (3) the algorithm is associated with a specific pathway that is presumed to be dysfunctional in women who go on to delivery spontaneous preterm—this opens the possibility of developing a therapeutic agent that can be paired with the diagnostic algorithm; (4) the invention allows for a single blood draw early in pregnancy to determine risk, which is an improvement upon the multi-step assessments that have traditionally been used; and (5) the timing of these methods at the beginning of the second trimester allow for timely implementation of clinical interventions for maximal benefit. The ideal service that would develop from this invention is a serologic test that could be offered to all pregnant women in the late first trimester or early second trimester to determine their risk of spontaneous preterm delivery. The development of a paired therapeutic option makes it more likely that clinicians who choose to use this invention are able to mitigate the biochemical pathway imbalance and reduce the tendency for spontaneous preterm delivery.

Other ROC curves were generated using the various steroids. For example, a ROC graph depicting the DOC/(16α-OHP and/or isopregnanolon) and spontaneous preterm birth (sPTB) at less than 32 weeks in Epoch 1 was generated.

Example 2

In this Example, the effect of altered mineralocorticoid/glucocorticoid (M/G) ratios on uterine contractility was analyzed. Smooth muscle contractility (including human myometrium) is dependent upon myosin light chain (MLC) phosphorylation, allowing for cross-bridge formation between myosin heads and actin filaments, which results in a contraction. Among intracellular signaling mechanisms, calcium signaling plays a primary role in activation of myosin light chain kinase, the enzyme responsible for phosphorylation of MLC. A gene expression array was used to target 92 genes involved in human intracellular calcium signaling (ThermoFisher) to delineate the influence of varying M/G ratios. Notably, women who delivered <30 weeks had an M/G ratio that approximated 1:10 in the cohort. Primary human myometrial cells were exposed to two ratios of M/G compounds (1:10, 1:2) and gene expression was compared to DMSO treated controls. Only a limited number of genes demonstrated >2-fold increase in expression with treatment (Table 2).

TABLE 2

Gene Expression Array Results with >2-fold change

| Gene | 1:10 M:G Ratio Fold-Change | 1:2 M:G Ratio Fold-Change |
|---|---|---|
| CALM2 | 12.150 | 11.054 |
| KRAS | 2.903 | 2.190 |
| QDPR | 2.111 | 2.174 |

The result of the experiment demonstrates a large increase in expression of CALM2, one of three distinct genes for production of calmodulin. Calmodulin is an essential intracellular calcium binding protein in all eukaryotes. In smooth muscle, calmodulin binding to calcium released from intracellular stores (store-operated calcium signaling) facilitates 8 activation of myosin light chain kinase and phosphorylation of MLC, leading to contractility. Modest increases in expression were observed for KRAS, an oncogene involved in cell division, and QDPR, which produces an enzyme involved in phenylalanine metabolism. Notably, expression of CALM2 rose with an increase in glucocorticoid concentration (decreased M/G ratio). In addition to the glucocorticoid stimulation of placental CRH production ("placental clock"), this data suggests a direct effect of increased glucocorticoid on calcium signaling which promotes uterine contractility.

Example 3

Figure 10:
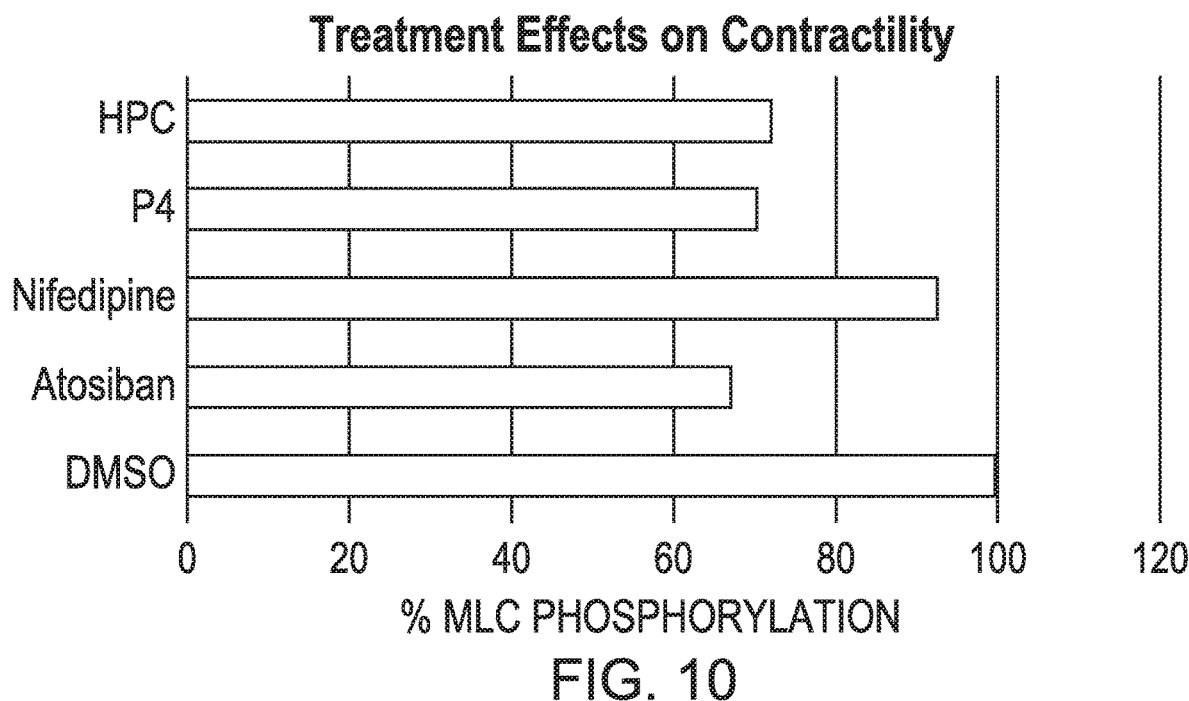
FIG. 10 depicts the effect of common PTB treatments on myometrial contractility as analyzed in Example 2.

In this Example, the ability of common clinical therapies to reduce myometrial contractility induced by the M/G ratio associated with early pre-term birth was analyzed. The ability of common clinical therapies to reduce myometrial contractility induced by the M/G ratio associated with early PTB was analyzed. Initial studies utilized an in-cell western (ICW) technique to explore the effects of commonly used medications in a high-throughput manner. The ICW assay has previously been validated for assessment of myometrial contractility by quantifying the phosphorylation of myosin light chain (MLC20), the final molecular step preceding contractility in human myometrial cells. An ICW assay was used to investigate the effects of 4 common tocolytics (progesterone, HPC, atosiban, nifedipine) in primary human myometrial cells treated with a 1:10 M/G ratio and stimulated with oxytocin (FIG. 10). MLC phosphorylation was seen to decrease approximately 35-40% with progesterone, HPC, and atosiban. Notably, the decline in MLC phosphorylation observed with Atosiban, an oxytocin receptor antagonist, was anticipated given the stimulation of contractility by oxytocin.

Figure 11:
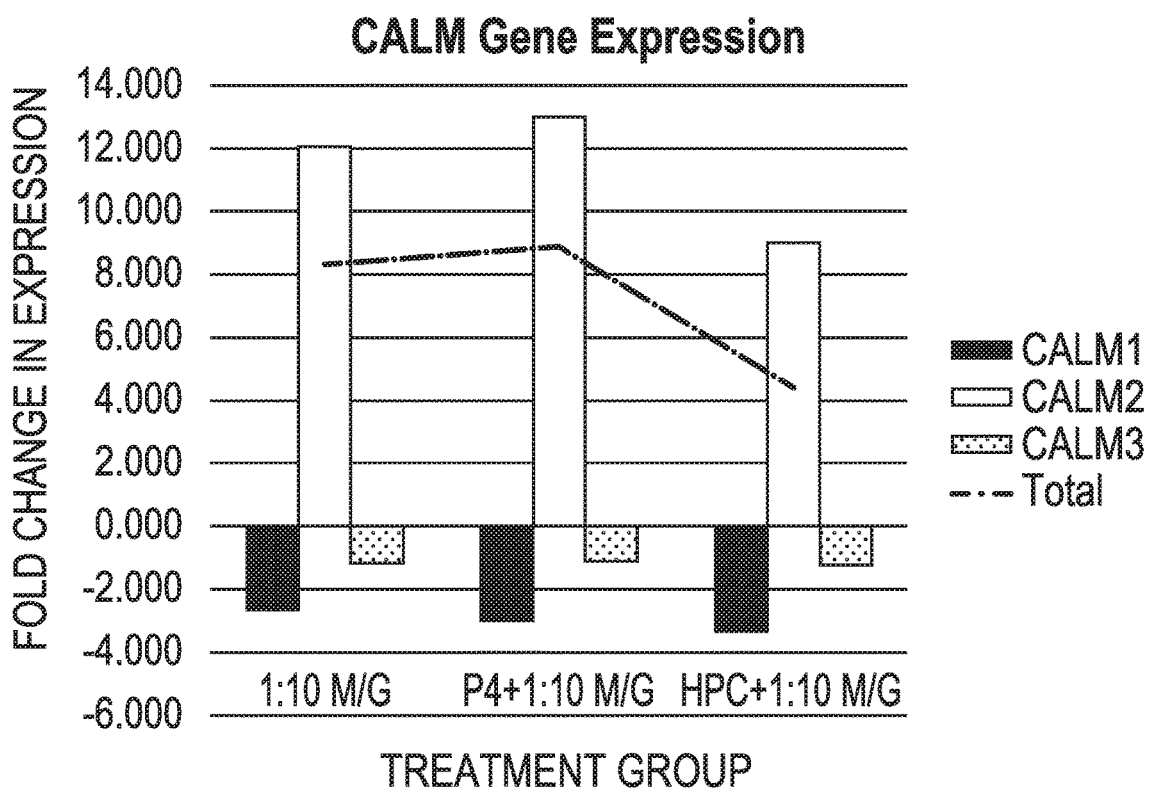
FIG. 11 depicts CALM gene expression with M/G exposure and progestogen treatment as analyzed in Example 3.

The effect of progesterone or HPC treatment on calmodulin gene expression (CALM1, CALM2, CALM3) was further explored. Primary myometrial cells were treated with a 1:10 M/G ratio and a gene array used to assess calmodulin expression. Compared to DMSO treated controls, both treatments demonstrated an increase in CALM2 with modest decreases in CALM1 and CALM3 (FIG. 11). However, HPC treatment resulted in only a 9-fold increase in CALM2 compared to a 13-fold increase in progesterone treated cells, translating to an ~30% reduction in expression. The fold change in total CALM expression (trend line for all three isoforms) was approximately half with HPC treatment (4.4-fold) compared to progesterone (8.9-fold) or control treatments (8.3-fold). These findings suggest that the decrease in MLC phosphorylation by HPC may be at least partially through a decrease in CALM2 expression, while progesterone acts through alternate mechanisms.

Summary. The culmination of the above Examples indicates that an imbalance in progesterone metabolism into the mineralocorticoid and glucocorticoid pathways increases the risk of spontaneous PTB<32 weeks by promoting myometrial contractility. Mechanistic elements of this relationship, including increases in pro-contractile molecules, are consistent with the maternal/fetal HPA axis phenotype of preterm birth. Evaluation of contemporary therapeutic options for PTB revealed that HPC has specificity to mitigate the specific pathways implicated by this phenotype, unlike progesterone, nifedipine, or atosiban. It has now been demonstrated that it is feasible to identify women with the maternal/fetal HPA axis phenotype of preterm birth using the DOC/16α-OHP biomarker as early as the late first trimester/early second trimester, allowing for timely intervention.

Clinical application. The phenotype of decreased M/G pathway activity is most predictive of women at risk for sPTB<32 weeks gestation. This population of births is smaller than the composite pool of preterm births<37 weeks; however, the resultant costs associated with medical care for the newborn are significantly higher. It is now believed that its unique biomarker algorithm (DOC/16α-OHP ratio) can be used as a general screening tool in all pregnancies to identify women at enhanced risk for uterine contractility.

What is claimed is:

1. A method for treating a pregnant female susceptible to spontaneous preterm delivery, the method comprising:
    determining a ratio of at least two steroids in the pregnant female by:
    obtaining a sample from the pregnant female;
    detecting a concentration of a first steroid selected from the group consisting of deoxycorticosterone, corticosterone, 18-hydroxycortiosterone, aldosterone, deoxycortisol, cortisol, and combinations thereof in the sample;
    detecting a concentration of at least a second steroid in the sample, wherein the second steroid is different from the first steroid; and
    detecting a ratio of the first steroid to the at least second steroid;
    if the ratio of the first steroid to the at least second steroid is less than 0.2, administering an effective amount of a compound selected from the group consisting of 17α-hydroxyprogesterone caproate (HPC), monohydroxylated HPC (HPC-OH), atosiban, nifedipine, terbutaline, eplerenone, allopregnanolone and derivatives thereof.

2. The method of claim 1, wherein the second steroid is selected from the group consisting of progesterone, 16α-hydroxyprogesterone, 6β-hydroxyprogesterone, 6α-hydroxyprogesterone, 17-hydroxyprogesterone, 11-deoxycortisol, cortisol, 11-deoxycorticosterone, 17-deoxycortisol, androstenedione, testosterone, estradiol, 20α-dihydroprogesterone, 17α,20α-dihydroxyprogesterone, isopregnanolone, and combinations thereof.

3. The method of claim 1, further comprising determining a concentration of a biomarker selected from the group consisting of insulin-like growth factor binding protein 4, sex-hormone binding globulin, lipopolysaccharide-binding protein (LBP), lipopolysaccharide binding protein (LBP) precursor, prothrombin (THRB), complement component C5 (C5 or CO5), plasminogen (PLMN), complement component C8 gamma chain (C8G or CO8G), Complement factor B, Ectonucleotide pyrophosphatase/phosphodiesterase family member 2, Gelsolin, N-acetylmuramoyl-L-alanine amidase, N-acetylmuramoyl-L-alanine amidase precursor, Hyaluronan-binding protein 2, BPI fold-containing family B member 1, complement component C8 alpha chain, apolipoprotein A-II, Ectonucleotide pyrophosphatase/phosphodiesterase family member 2, profiling-1, pro-neuropeptide Y, complement component C8 beta chain, coagulation factor XIII B chain, N-acetylmuramoyl-L-alanine amidase, inter-alpha-trypsin inhibitor heavy chain H4, inter-alpha-trypsin inhibitor heavy chain H3 preproprotein, leucyl-cystinyl aminopeptidase, alpha-2-HS-glycoprotein, 5'-AMP-activated protein kinase subunit gamma-3, afamin precursor, alpha-1-antichymotrypsin precursor, alpha-1B- glycoprotein precursor, alpha-2-antiplasmin isoform a precursor, alpha-2-HS-glycoprotein preproprotein, alpha-2-HS-macroglobulin precursor, angiotensinogen preproprotein, antithrombin-III precursor, apolipoprotein A-II preproprotein, apolipoprotein A-IV precursor, apolipoprotein B-100 precursor, apolipoprotein C-I precursor, apolipoprotein C-II precursor, apolipoprotein C-III precursor, apolipoprotein E precursor, ATP-binding cassette sub-family D member 4, ATP-binding cassette sub-family F member 3, beta-2-glycoprotein 1 precursor, beta-Ala-His dipeptidase precursor, biotinidase precursor, carboxypeptidase B2 preproprotein, carboxypeptidase N catalytic chain precursor, carboxypeptidase N subunit 2 precursor, catalase, ceruloplasmin precursor, cholinesterase precursor, clusterin preproprotein, coagulation factor IX preproprotein, coagulation factor VII isoform a, coagulation factor VII isoform a preproprotein, coagulation factor X preproprotein, coagulation factor XIII B chain, coiled-coil domain-containing protein 13, complement C1q subcomponent subunit A precursor, complement C1q subcomponent subunit B precursor, complement C1q subcomponent subunit C precursor, complement C1r subcomponent precursor, complement C1s subcomponent precursor, complement C2 isoform 3, complement C3 precursor, complement C4-A isoform 1, complement C5 preproprotein, component C6 precursor, component C7 precursor, component C8 alpha chain precursor, complement component C9 precursor, complement factor B preproprotein, complement factor H isoform a precursor, complement factor H isoform b precursor, complement factor H H-related protein 1 precursor, complement factor I preproprotein, conserved oligomeric Golgi complex subunit 6 isoform, corticosteroid-binding globulin precursor, C-reactive protein precursor, dopamine beta-hydroxylase precursor, double-stranded RNA-specific editase B2, dual oxidase 2 precursor, FERM domain-containing protein 8, fetuin-B precursor, ficolin-3 isoform 1 precursor, gastric intrinsic factor precursor, gelsolin isoform d, glutathione peroxidase 3 precursor, hemopexin precursor, heparin cofactor 2 precursor, hepatocyte cell adhesion molecule precursor, hepatocyte growth factor activator preproprotein, histidine-rich glycoprotein precursor, hyaluronan-binding protein 2 isoform 1 preproprotein, inactive caspase-12 insulin-degrading enzyme isoform 1, insulin-like growth factor-binding protein complex acid labile subunit isoform 2 precursor, inter-alpha-trypsin inhibitor heavy chain H1 isoform a precursor, inter-alpha-trypsin inhibitor heavy chain H2 precursor, inter-alpha-trypsin inhibitor heavy chain H4 isoform 1 precursor, kallistatin precursor, kininogen-1 isoform 2 precursor, leucine-rich alpha-2-glycoprotein precursor, lumican precursor, m7GpppX diphosphatase, matrix metalloproteinase-19 isoform 1 preproprotein, MBT domain-containing protein 1, monocyte differentiation antigen CD14 precursor, pappalysin-1 preproprotein, phosphatidylinositol-glycan-specific phospholipase D precursor, pigment epithelium-derived factor precursor, plasma kallikrein preproprotein, plasma protease C1 inhibitor precursor, plasminogen isoform 1 precursor, platelet basic protein preproprotein, platelet glycoprotein V precursor, pregnancy zone protein precursor, pregnancy-specific beta-1-glycoprotein 5, pregnancy-specific beta-1-glycoprotein 5 precursor, pregnancy-specific beta-1-glycoprotein 6, pregnancy-specific beta-1-glycoprotein 6 precursor, pregnancy-specific beta-1-glycoprotein 7, pregnancy-specific beta-1-glycoprotein 8, pregnancy-specific beta-1-glycoprotein 9, pregnancy-specific beta-1-glycoprotein 11, pregnancy-specific beta-1-glycoprotein 2, pregnancy-specific beta-1-glycoprotein 3, pregnancy-specific beta-1-glycoprotein 4, progesterone-induced-blocking factor 1, protein AMBP preproprotein, protein CBFA2T2 isoform MTGR1b, protein FAM98C, protein NLRC3, protein Z-dependent protease inhibitor precursor, prothrombin preproprotein, putative hydroxypyruvate isomerase isoform 1, ras-like protein family member 10A precursor, ras-related GTP-binding protein A, retinol-binding protein 4 precursor, sex hormone-binding globulin isoform 1 precursor, sex hormone-binding globulin isoform 4 precursor, signal transducer and activator of transcription 2, spectrin beta chain non-erythrocytic 1, stabilin-1 precursor, succinate semialdehyde dehydrogenase mitochondrial, tetranectin precursor, THAP domain-containing protein 6, thyroxine-binding globulin precursor, tripartite motif-containing protein 5, vitamin D-binding protein isoform 1 precursor, vitronectin precursor, zinc finger protein 142, attractin isoform 2 preproprotein, transforming growth factor-beta-induced protein ig-h3 precursor, transthyretin precursor, uncharacterized protein C3orf20, beta-2-microglobulin precursor, bone marrow proteoglycan isoform 1 preproprotein, chorionic gonadotropin beta polypeptide 8 precursor, chorionic somatomammotropin hormone 2 isoform 2 precursor, macrophage colony-stimulating factor 1 receptor precursor, zinc-alpha-2-glycoprotein precursor, PAN-PSG, complement component C6 precursor, EGF-containing fibulin-like extracellular matrix protein 1, disintegrin and metalloproteinase domain-containing protein 12, and combinations thereof.

4. The method of claim 1, further comprising detecting a first concentration of at least one of calmodulin 1 (CALM1), calmodulin 2 (CALM2), and calmodulin 3 (CALM3) prior to administering the compound, and detecting at least a second concentration of at least one of CALM1, CALM2 and CALM3 after administration of the compound, and wherein a decrease in the second concentration of one or more of CALM1, CALM2, and CALM3 indicates the pregnant female is effectively being treated.

5. The method of claim 1, further comprising detecting a first concentration of at least one of calmodulin 1 (CALM1), calmodulin 2 (CALM2), and calmodulin 3 (CALM3) prior to administering the compound, and detecting at least a second concentration of at least one of CALM1, CALM2 and CALM3 after administration of the compound, and wherein an increase in the second concentration of one or more of CALM1, CALM2, and CALM3 indicates a need to continue administration of the compound to the pregnant female.

6. The method of claim 1, further comprising determining a change in a concentration of a nucleic acid.

7. The method of claim 6, where the nucleic acid is at least one of cell free plasma (CFP) RNA or cell free fetal DNA.

8. The method of claim 1, wherein the first steroid is deoxycorticosterone (DOC) and the second steroid is 16α-hydroxyprogesterone (16αOHP).

9. The method of claim 8, wherein the concentration of DOC is determined using an assay that contacts the sample with an antibody, wherein the antibody specifically binds to DOC.

10. The method of claim 8, wherein the concentration of 16αOHP is determined using an assay that contacts the sample with an antibody that specifically binds to 16αOHP.

11. The method of claim 1, wherein the first steroid is deoxycorticosterone (DOC) and the second steroid is isopregnanolone.

12. The method of claim 1, further comprising analyzing at least one risk factor selected from the group consisting of: age, race, medication exposure, prior pregnancy, history of previous low birth weight or preterm delivery, multiple 2nd trimester spontaneous abortion, prior first trimester induced abortion, preeclampsia, familial and intergenerational factors, history of infertility, nulliparity, placental abnormalities, cervical and uterine anomalies, gestational bleeding, intrauterine growth restriction, in utero diethylstilbestrol exposure, multiple gestations, infant sex, short stature, low prepregnancy weight/low body mass index, diabetes, hypertension, hypothyroidism, asthma, education level, tobacco use, urogenital infections, activity levels, sleep quality, and combinations thereof.

13. The method of claim 1, wherein the first steroid is deoxycorticosterone (DOC) and the second steroid is 11-deoxycortisol.

14. The method of claim 13, wherein the concentration of DOC is determined using an assay that contacts the sample with an antibody that specifically binds to DOC, and the concentration of 11-deoxycortisol is determined using an assay that contacts the sample with an antibody that specifically binds to 11-deoxycortisol.

15. The method of claim 1, wherein the compound is administered to the pregnant female after 10 weeks of gestation.

16. The method of claim 1, wherein the compound is administered to the pregnant female after 12 weeks of gestation.

17. The method of claim 1, wherein the compound is administered to the pregnant female at or after 16 weeks gestation.

18. The method of claim 1, wherein the sample is obtained at less than 32 weeks.

19. The method of claim 1, wherein the sample is selected from a plasma sample, a serum sample, a whole blood sample, a salivary sample, and a urine sample.

20. The method of claim 1, further comprising administering or modifying a life factor selected from exercise regimen, dietary regimen, sleep patterns, and smoking cessation.

* * * * *